(12) United States Patent
Moshashaee et al.

(10) Patent No.: US 11,345,904 B2
(45) Date of Patent: May 31, 2022

(54) TARGETED THERAPEUTIC LYSOSOMAL ENZYME FUSION PROTEINS, ASSOCIATED FORMULATIONS AND USES THEREOF

(71) Applicant: BIOMARIN PHARMACEUTICAL INC., Novato, CA (US)

(72) Inventors: Saeed Moshashaee, Novato, CA (US); Jason K. Pinkstaff, Novato, CA (US); Adam Shaywitz, Novato, CA (US); Natalie Ciaccio, Novato, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 347 days.

(21) Appl. No.: 16/078,546

(22) PCT Filed: Feb. 24, 2017

(86) PCT No.: PCT/US2017/019343
§ 371 (c)(1),
(2) Date: Aug. 21, 2018

(87) PCT Pub. No.: WO2017/147414
PCT Pub. Date: Aug. 31, 2017

(65) Prior Publication Data
US 2020/0297821 A1 Sep. 24, 2020

Related U.S. Application Data

(60) Provisional application No. 62/299,188, filed on Feb. 24, 2016, provisional application No. 62/428,221, filed on Nov. 30, 2016.

(51) Int. Cl.
| | | |
|---|---|---|
| *C12N 9/26* | (2006.01) | |
| *C12N 9/24* | (2006.01) | |
| *A61K 47/65* | (2017.01) | |
| *A61P 25/28* | (2006.01) | |
| *A61K 9/00* | (2006.01) | |
| *A61K 38/43* | (2006.01) | |
| *A61K 47/26* | (2006.01) | |

(52) U.S. Cl.
CPC .......... *C12N 9/2402* (2013.01); *A61K 9/0019* (2013.01); *A61K 38/43* (2013.01); *A61K 47/26* (2013.01); *A61K 47/65* (2017.08); *A61P 25/28* (2018.01)

(58) Field of Classification Search
CPC .................................................... C12N 9/2402
See application file for complete search history.

(56) References Cited

U.S. PATENT DOCUMENTS

| | | | |
|---|---|---|---|
| 6,534,300 B1 | 3/2003 | Canfield | |
| 6,537,785 B1 | 3/2003 | Canfield | |
| 9,376,480 B2* | 6/2016 | Aoyagi-Scharber | .... A61P 43/00 |
| 9,771,408 B2* | 9/2017 | Aoyagi-Scharber | .... A61P 43/00 |
| 9,834,587 B2* | 12/2017 | Aoyagi-Scharber | ... C07K 14/65 |
| 9,834,588 B2* | 12/2017 | Aoyagi-Scharber | ......................... C12Y 302/0105 |
| 9,845,346 B2* | 12/2017 | Aoyagi-Scharber | ......................... C12Y 302/0105 |
| 10,301,369 B2* | 5/2019 | Aoyagi-Scharber | ......................... C12Y 302/0105 |
| 2013/0295077 A1 | 11/2013 | Concino et al. | |
| 2014/0161788 A1* | 6/2014 | Aoyagi-Scharber | ......................... C12N 9/2402 424/94.61 |
| 2014/0249072 A1* | 9/2014 | Chen | ...................... A61P 37/00 514/1.4 |
| 2019/0225666 A1* | 7/2019 | Aoyagi-Scharber | .... A61P 43/00 |

FOREIGN PATENT DOCUMENTS

| | | |
|---|---|---|
| CN | 101084015 A | 12/2007 |
| CN | 101903030 A | 12/2010 |
| CN | 102695499 A | 9/2012 |
| JP | 201 3542913 A | 11/2013 |
| WO | 2010148253 A2 | 12/2010 |
| WO | WO-2010148253 A2 | 12/2010 |
| WO | 2011163649 A2 | 12/2011 |
| WO | WO-2011163649 A2 | 12/2011 |
| WO | WO-2011163652 A2 | 12/2011 |
| WO | 2014085621 A1 | 6/2014 |
| WO | WO-2014085621 A1 | 6/2014 |
| WO | WO-2017147414 A1 | 8/2017 |

OTHER PUBLICATIONS

Studer. Residue mutations and their impact on protein structure and function: detecting beneficial and pathogenic changes. Biochem. J. (2013) 449, 581-594.*
Altschul et al. Basic Local Alignment Search Tool. J. Mol. Biol. 215: 403-410 (1990).
Altschul, et al. Gapped BLAST and PSI-BLAST: a new generation of protein database search programs. Nucleic Acids Res 25:3389-3402 (1977).
Anonymous. ACSF recipes. Retrieved from the Internet: URL:https://clampthis.files.wordpress.com/2011/10/acsf-recipes.pdf (2011).
Beniaminovitz et al. Prevention of rejection in cardiac transplantation by blockade of the interleukin-2 receptor with a monoclonal antibody. N. Engl J. Med. 342:613-619 (2000).
Berard et al. A review of interleukin-2 receptor antagonists in solid organ transplantation. Pharmacotherapy 19:1127-1137 (1999).
Bobo et al. Convection-enhanced delivery of macromolecules in the brain. PNAS USA 91:2076-2080 (1994).
Branco et al. Selective deletion of antigen-specific, activated T cells by a humanized MAB to CD2 (MEDI-507) is mediated by NK cells. Transplantation 68:1588-1596 (1999).
Carpenter et al. Chapter 5: Rational Design of Stable Lyophilized Protein Formulations: Theory and Practice. In Rational Design of Stable Protein Formulations (pp. 109-133) (2002).

(Continued)

*Primary Examiner* — Yong D Pak
(74) *Attorney, Agent, or Firm* — Wilson Sonsini Goodrich & Rosati

(57) ABSTRACT

The present disclosure relates in general to therapeutic lysosomal enzyme fusion proteins useful for treating lysosomal storage diseases, liquid formulations comprising such fusion proteins and associated methods useful for treating lysosomal storage diseases in mammals.

20 Claims, 13 Drawing Sheets

Specification includes a Sequence Listing.

(56) References Cited

OTHER PUBLICATIONS

Chi. Excipients and their Effects on the Quality of Biologies. Retrieved from the Internet: URL:https://www.aaps.org/uploadedFiles/Content/Sections_and_Groups/Sections/Formulation_Design_And_Development_Section/FDDTechCornerMay2012.pdf [retrieved on May 19, 2016].
Chirmule et al. Readministration of adenovirus vector in nonhuman primate lungs by blockade of CD40-CD40 ligand interactions. J. Virol. 74:3345-3352 (2000).
Costantino et al. Deterioration of Lyophilized Pharmaceutical Proteins. Biochemistr 63(3):422-429 (1998).
Dekaban. Changes in brain weights during the span of human life: relation of brain weights to body heights and body weights. Ann Neurol 4:345-56 (1978).
Dominiquez et al. Liposomal cytarabine (DepoCyte) for the treatment of neoplastic meningitis. Clin Transl Oncol 7(6):232-238 (2005).
Eckhoff et al. The safety and efficacy of a two-dose daclizumab (zenapax) induction therapy in liver transplant recipients. Transplantation 69:1867-1872 (2000).
Eisenach et al. Phase I safety assessment of intrathecal ketorolac. Pain 99:599-604 (2002).
Ekberg et al. Daclizumab prevents acute rejection and improves patient survival post transplantation: 1 year pooled analysis. Transpl. Int. 13:151-159 (2000).
Fishwild et al. Differential effects of administration of a human anti-CD4 monoclonal antibody, HM6G, in nonhuman primates. Clin. Immunol. 92:138-152 (1999).
Gaziev et al. Chronic graft-versus-host disease: is there an alternative to the conventional treatment? Bone Marrow Transplant. 25:689-696 (1999).
Gill et al. Direct brain infusion of glial cell line-derived neurotrophic factor in Parkinson disease. Nature Medicine 9(5):589-95 (2003).
Graham et al. Characteristics of a human cell line transformed by DNA from human adenovirus type 5. J. Gen. Virol. 36:59-72 (1977).
Grondin et al. Chronic, controlled GDNF infusion promotes structural and functional recovery in advanced parkinsonian monkeys. Brain 125(Pt 10):2191-201 (2012).
Grouls et al. Chapter 15: General considerations in the formulation of drugs for spinal delivery. Spinal Drug Delivery, Elsevier Science (Yaksh, TL ed.) (1999).
Gummert et al. Newer immunosuppressive drugs: a review. J. Am. Soc. Nephrol. 10:1366-1380 (1999).
Henry. Cyclosporine and tacrolimus (FK506): a comparison of efficacy and safety profiles. Clin. Transplant. 13:209-220 (1999).
Hong et al. Immunosuppressive agents in organ transplantation: past, present, and future. Semin. Nephrol. 20:108-125 (2000).
Hood et al. Phase I safety assessment of intrathecal neostigmine methylsulfate in humans. Anesthesiology 82(2): 331-43 (1995).
Ideguchi et al. Local adenovirus-mediated CTLA4-immunoglobulin expression suppresses the immune responses to adenovirus vectors in the brain. Neuroscience 95:217-226 (2000).
Ito et al. Induction of CTL responses by simultaneous administration of liposomal peptide vaccine with anti-CD40 and anti-CTLA-4 mAb. J. Immunol. 164:1230-1235 (2000).
Jain et al. Effect of trehalose on protein structure. Protein Science 18(1):24-36 (2009).
Johanson et al. Multiplicity of cerebrospinal fluid functions: New challenges in health and disease. Cerebrospinal Fluid Res. 5:10 (2008).
Kerwin. Polysorbates 20 and 80 used in the formulation of protein biotherapeutics: Structure and degradation pathways. J Pharm Sci 97(8):2924-2935 (2008).
Kim et al. Extended CSF cytarabine exposure following intrathecal administration of DTC 101. J. Clin. Oncology 11(11):2186-2193 (1993).
King et al. Prolongation of epidural bupivacaine analgesia with glycerin. Can J Anaesth 40(5):431-434 (1993).
Kolodny et al. Storage Diseases of the Reticuloendothelial System, In: Nathan and Oski's Hematology of Infancy and Childhood, 5th ed., vol. 2, David G. Nathan and Stuart H. Orkin, Eds., W. B. Saunders Co., pp. 1461-1507 (1998).
Kroin. Intrathecal drug administration. Present use and future trends. Clin Pharmacokinet 22(5):319-326 (1992).
Kurlberg et al. Blockade of the B7-CD28 pathway by CTLA4-lg counteracts rejection and prolongs survival in small bowel transplantation. Scand. J. Immunol. 51:224-230 (2000).
Lazorthes et al. Advances in Drug Delivery Systems and Applications in Neurosurgery. Adv Tech Stand Neurosurg. 18:143-192 (1991).
Marinova-Mutafchieva et al. A comparative study into the mechanisms of action of antitumor necrosis factor alpha, anti-CD4, and combined anti-tumor necrosis factor alpha/anti-CD4 treatment in early collagen-induced arthritis. Arthritis Rheum. 43:638-644 (2000).
Mather et al. Culture of testicular cells in hormone-supplemented serum-free medium. Annals N.Y. Acad. Sci. 383:44-68 (1982).
Moder. New medications for use in patients with rheumatoid arthritis. Ann. Allergy Asthma Immunol. 84:280-284 (2000).
Nail et al. Fundamentals of freeze-drying, in Development and manufacture of protein pharmaceuticals. Nail S.L. editor New York: Kluwer Academic/Plenum Publishers, pp. 281-353 (2002).
Nayar et al. Rational Designe of Stable Protein Formulations. FP1-2, 177-198 (2002).
Nevins. Overview of new immunosuppressive therapies. Curr. Opin. Pediatr. 12:146-150 (2000).
Nguyen et al. Convective distribution of macromolecules in the primate brain demonstrated using computerized tomography and magnetic resonance imaging. J. Neurosurg. 98:584-590 (2003).
Nutt et al. Randomized, double-blind trial of glial cell line-derived neurotrophic factor (GDNF) in PD. Neurology 60:69-73 (2003).
Ommaya et al. Implantable devices for chronic access and drug delivery to the central nervous system. Cancer Drug Delivery 1:169-179 (1984).
PCT/US2017/019343 International Search Report and Written Opinion dated Jul. 28, 2017.
Ponticelli et al. Promising new agents in the prevention of transplant rejection. Drugs R. D. 1:55-60 (1999).
Potter et al. Review—the use of immunosuppressive agents to prevent neutralizing antibodies against a transgene product Ann. N.Y. Acad. Sci. 875:159-174 (1999).
Przepiorka et al. A phase II study of BTI-322, a monoclonal anti-CD2 antibody, for treatment of steroid-resistant acute graft-versus-host disease. Blood 92:4066-4071 (1998).
Qi et al. Effect of tacrolimus (FK506) and sirolimus (rapamycin) mono- and combination therapy in prolongation of renal allograft survival in the monkey. Transplantation 69:1275-1283 (2000).
Rane et al. Intrathecal adenosine administration: a phase 1 clinical safety study in healthy volunteers, with additional evaluation of its influence on sensory thresholds and experimental pain. Anesthesiology 89(5):1108-1115 (1998).
Sakura et al. The addition of phenylephrine contributes to the development of transient neurologic symptoms after spinal anesthesia with 0.5% tetracaine. Anesthesiology 87(4):771-8 (1997).
Shiobara. Development of Artificial Cerebrospinal Fluid: Basic Experiments, and Phase II and III Clinical Trials. J Neurol Neurophysiol 4:5 (2013).
Shulman et al. Effect of epidural and subarachnoid injections of a 10% butamben suspension. Reg Anesth 15(3): 142-6 (1990).
Shulman et al. Nerve blocks with 5% butamben suspension for the treatment of chronic pain syndromes. Reg Anesth Pain Med 23(4):395-401 (1998).
Slavik et al. CD28/CTLA-4 and CD80/CD86 families: signaling and function. Immunol. Res. 19:1-24 (1999).
Stevens et al. Back pain after epidural anesthesia with chloroprocaine. Anesthesiology 78(3):492-497 (1993).
Tang et al. Design of freeze-drying processes for pharmaceuticals: Practical advice. Pharm. Res. 21:191-200 (2004).
Urlaub et al. Isolation of Chinese hamster cell mutants deficient in dihydrofolate reductase activity. PNAS USA 77:4216-4220 (1980).
Von Specht et al. Enzyme replacement in Tay-Sachs disease. Neurology 29:848-854 (1979).

(56) References Cited

OTHER PUBLICATIONS

Wang. Lyophilization and development of solid protein pharmaceuticals. Int. J. Pharm., 203(1-2): 1-60 (2000).
Williams et al. The lyophilization of pharmaceuticals: A literature review. J Parenteral Sei. Technol. 38:48-59 (1984).
Wiseman et al. Daclizumab: a review of its use in the prevention of acute rejection in renal transplant recipients. Drugs 58:1029-1042 (1999).
Jain, N.J. et al., "Effect of trehalose on protein structure," Protein Science, vol. 18, No. 1, Jan. 1, 2009, pp. 24-36.
Rajiv, N. et al., "Rational Designe of Stable Protein Formulations," In: Rational Designe of Stable Protein Formulations, Jan. 1, 2002, Kluwer Academic, p. FP1-2, vol. 160, pp. 177-181 and pp. 186-188.
Eva, Y. Chi: "Excipients and their Effects on the Quality of Biologics," Internet Citation, Apr. 14, 2012, pp. 1-9.
Kerwin, B. A., "Polysorbates 20 and 80 used in the formulation of protein biotherapeutics: Structure and degradation pathways," Journal of Pharmaceutical Sciences, vol. 97, No. 8, Aug. 1, 2008, pp. 2924-2935.
Anonymous: ACSF recipes, Oct. 26, 2011, pp. 1-10.
Ryuzo, S., "Development of Artificial Cerebrosphinal Fluid: Basic Experiments, and Phase II and III Clinical Trials," Journal of Neurology & Neurophysiology, vol. 4, No. 5, Jan. 1, 2013.
International Search Report and Written Opinion for corresponding PCT/US2017/019343, dated Jul. 28, 2017 (35 pages).
Beesley et al. Molecular defects in Sanfilippo syndrome type B (mucopolysaccharidosis PN). Journal of inherited metabolic disease 28(5):759-767 (2005).
Boustany. Lysosomal storage diseases—the horizon expands. Nature Reviews Neurology 9(10):583-598 (2013).
Carpenter et al. Long-term storage of proteins. Curr Protoc Protein Sci Chapter 4:Unit 4.6 (2002).
Chen et al. Fusion protein linkers: Property, design and functionality. Advanced Drug Delivery Reviews 65:1357-1369 (2013).
Jahn et al. How to systematically the evaluate immunogenicity of therapeutic proteins—regulatory considerations. New Biotechnology 25(5):280-286 (2009).
Maeda et al. Engineering of functional chimeric protein G-Vargula Luciferase. Analytical biochemistry 249(2):147-152 (1997).
Ortolano et al. Treatment of lysosomal storage diseases: recent patents and future strategies. Recent Pat Endocr Metab Immune Drug Discov 8(1):9-25 (2014).
Pakula et al. Genetic Analysis of Protein Stability and Function. Annu. Rev. Genet. 23:289-310 (1989).
Pastores et al. Current and emerging therapies for the lysosomal storage disorders Expert Opin Emerg Drugs 10(4):891-902 (2005).
Bhandari et al. Solubility-Weighted Index: fast and accurate prediction of protein solubility. Bioinformatics 36(18):4691-4698 (2020).
Chen et al. Fusion Protein Linkers: Property, Design and Functionality. Adv Drug Deliv Rev 65:1357-1369 (2013). Available online Sep. 29, 2012.
Life Science Project—0.2 sodium phosphate buffer dated Oct. 22, 2011 [retrieved Aug. 16, 2021], retrieved from the internet: < url: < a href="https://life-science-project.com/469/" > https://life-science-project.com/469/ (Machine translation) < /url: < a > .
Meijer et al. Residual N-acetyl-α-glucosaminidase activity in fibroblasts correlates with disease severity in patients with mucopolysaccharidosis type IIIB. J Inherit Metab Dis 39(3):437-445 (2016).
Valstar et al. Mucopolysaccharidosis type IIIB may predominantly present with an attenuated clinical phenotype. J Inherit Metab Dis 33(6):759-67 (2010).
Weber et al. Sanfilippo type B syndrome (mucopolysaccharidosis III B): allelic heterogeneity corresponds to the wide spectrum of clinical phenotypes. Eur J Hum Genet 7(1):34-44 (1999).

\* cited by examiner

Figure 1

DEAREAAAVRALVARLLGPGPAADFSVSVERALAAKPGLDTYSLGGGGAARVRVRGST
GVAAAAGLHRYLRDFCGCHVAWSGSQLRLPRPLPAVPGELTEATPNRYRYYQNVCTQS
YSFVWWDWARWEREIDWMALNGINLALAWSGQEAIWQRVYLALGLTQAEINEFFTG
PAFLAWGRMGNLHTWDGPLPPSWHIKQLYLQHRVLDQMRSFGMTPVLPAFAGHVPE
AVTRVFPQVNVTKMGSWGHFNCSYSCSFLLAPEDPIFPIIGSLFLRELIKEFGTDHIYGAD
TFNEMQPPSSEPSYLAAATTAVYEAMTAVDTEAVWLLQGWLFQHQPQFWGPAQIRA
VLGAVPRGRLLVLDLFAESQPVYTRTASFQGQPFIWCMLHNFGGNHGLFGALEAVNGG
PEAARLFPNSTMVGTGMAPEGISQNEVVYSLMAELGWRKDPVPDLAAWVTSFAARRY
GVSHPDAGAAWRLLLRSVYNCSGEACRGHNRSPLVRRPSLQMNTSIWYNRSDVFEAW
RLLLTSAPSLATSPAFRYDLLDLTRQAVQELVSLYYEEARSAYLSKELASLLRAGGVLAYELLP
ALDEVLASDSRFLLGSWLEQARAAAVSEAEADFYEQNSRYQLTLWGPEGNILDYANKQL
AGLVANYYTPRWRLFLEALVDSVAQGIPFQQHQFDKNVFQLEQAFVLSKQRYPSQPRG
DTVDLAKKIFLKYYPRWVAGSW (SEQ ID NO:1)

Figure 2

DEAREAAAVRALVARLLGPGPAADFSVSVERALAAKPGLDTYSLGGGGAARVRVRGST
GVAAAAGLHRYLRDFCGCHVAWSGSQLRLPRPLPAVPGELTEATPNRYRYYQNVCTQS
YSFVWWDWARWEREIDWMALNGINLALAWSGQEAIWQRVYLALGLTQAEINEFFTG
PAFLAWGRMGNLHTWDGPLPPSWHIKQLYLQHRVLDQMRSFGMTPVLPAFAGHVPE
AVTRVFPQVNVTKMGSWGHFNCSYSCSFLLAPEDPIFPIIGSLFLRELIKEFGTDHIYGAD
TFNEMQPPSSEPSYLAAATTAVYEAMTAVDTEAVWLLQGWLFQHQPQFWGPAQIRA
VLGAVPRGRLLVLDLFAESQPVYTRTASFQGQPFIWCMLHNFGGNHGLFGALEAVNGG
PEAARLFPNSTMVGTGMAPEGISQNEVVYSLMAELGWRKDPVPDLAAWVTSFAARRY
GVSHPDAGAAWRLLLRSVYNCSGEACRGHNRSPLVRRPSLQMNTSIWYNRSDVFEAW
RLLLTSAPSLATSPAFRYDLLDLTRQAVQELVSLYYEEARSAYLSKELASLLRAGGVLAYELLP
ALDEVLASDSRFLLGSWLEQARAAAVSEAEADFYEQNSRYQLTLWGPEGNILDYANKQL
AGLVANYYTPRWRLFLEALVDSVAQGIPFQQHQFDKNVFQLEQAFVLSKQRYPSQPRG
DTVDLAKKIFLKYYPRWVAGSWGAPGGGSPAPAPTPAPAPTPAPAGGGPSGAPLCGGE
LVDTLQFVCGDRGFYFSRPASRVSARSRGIVEECCFRSCDLALLETYCATPAKSE (SEQ ID
NO:5)

Figure 3
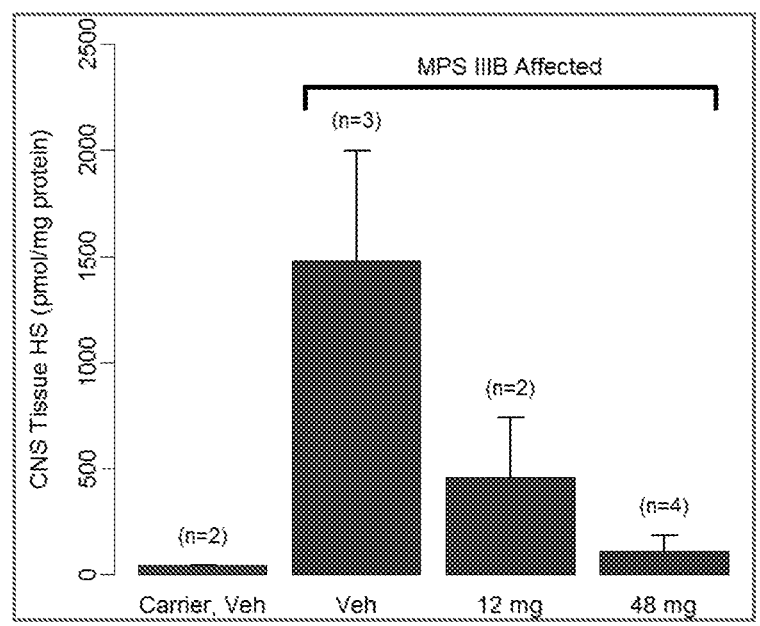
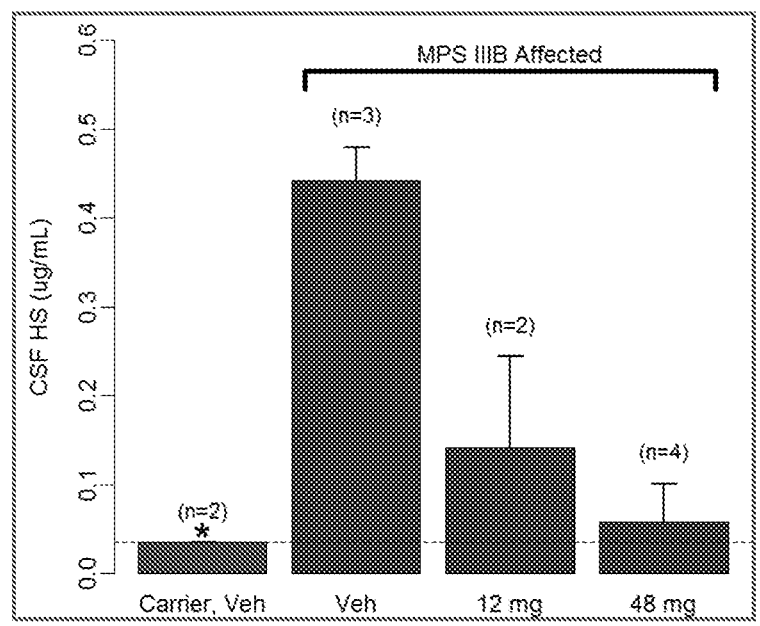

Figure 10
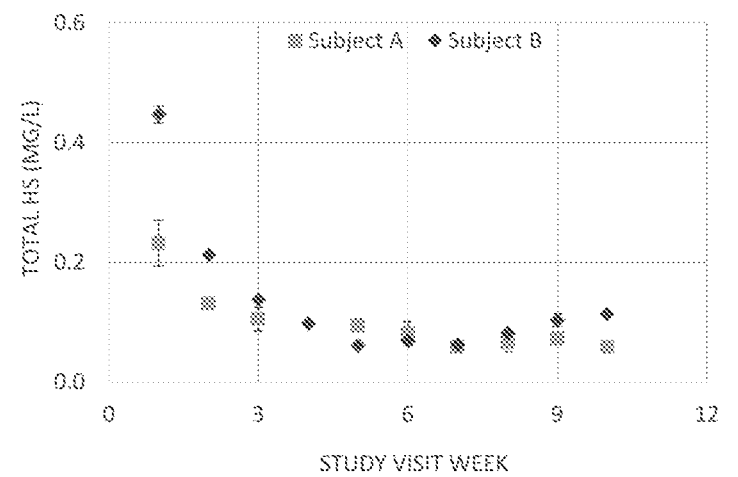
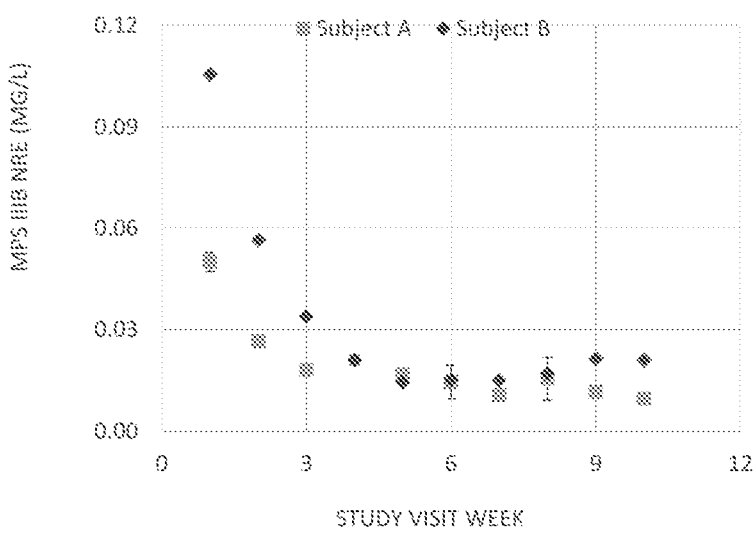

TARGETED THERAPEUTIC LYSOSOMAL ENZYME FUSION PROTEINS, ASSOCIATED FORMULATIONS AND USES THEREOF

CROSS REFERENCE TO RELATED APPLICATIONS

This application is the U.S. national phase application, pursuant to 35 U.S.C. § 371, of PCT International Application Ser. No.: PCT/US2017/019343, filed Feb. 24, 2017, designating the United States and published in English, which claims the benefit of the following U.S. Provisional Application Nos. 62/299,188, filed Feb. 24, 2016 and 62/428,221, filed Nov. 30, 2016; respectively. The entire contents of which are incorporated herein by reference.

FIELD OF THE DISCLOSURE

The present disclosure relates, in general, to therapeutic lysosomal enzyme fusion proteins useful for treating lysosomal storage diseases, formulations comprising such therapeutic lysosomal enzyme fusion proteins and associated methods for treating lysosomal storage diseases in mammals.

BACKGROUND

Normally, mammalian lysosomal enzymes are synthesized in the cytosol and traverse the ER where they are glycosylated with N-linked, high mannose type carbohydrate. In the golgi, the high mannose carbohydrate is modified on lysosomal enzymes by the addition of mannose-6-phosphate (M6P) which targets these proteins to the lysosome. The M6P-modified enzymes are then delivered to the lysosome via interaction with either/both of two M6P receptors.

More than forty lysosomal storage diseases (LSDs) are caused, directly or indirectly, by the absence of one or more lysosomal enzymes in the lysosome. Enzyme replacement therapy for LSDs is being actively pursued. Therapy generally requires that LSD proteins be taken up and delivered to the lysosomes of a variety of cell types in an M6P-dependent fashion. One possible approach involves purifying an LSD protein and modifying it to incorporate a carbohydrate moiety with M6P. This modified material may be taken up by the cells more efficiently than unmodified LSD proteins due to interaction with M6P receptors on the cell surface.

A peptide-based targeting technology that allows more efficient delivery of therapeutic enzymes to the lysosomes has been previously developed. This proprietary technology is termed Glycosylation Independent Lysosomal Targeting (GILT) because a peptide tag that is linked to the therapeutic enzyme replaces M6P as the moiety that targets the protein to the lysosomes. Details of the GILT technology are described in U.S. Application Publication Nos. 2003-0082176, 2004-0006008, 2003-0072761, 2005-0281805, 2005-0244400, U.S. Pat. Nos. 8,492,337 and 8,563,691, and International Publications WO 03/032913, WO 03/032727, WO 02/087510, WO 03/102583, WO 2005/078077, WO 2009/137721 and WO 2014/085621, the disclosures of all of which are hereby incorporated by reference.

SUMMARY OF THE DISCLOSURE

The present disclosure provides further improved compositions, formulations and methods for efficient lysosomal targeting of therapeutic fusion proteins based on the GILT technology. Among other things, the present disclosure provides methods and compositions for targeting therapeutic lysosomal enzymes to lysosomes using lysosomal targeting peptides for the treatment of lysosomal storage disorders. The present disclosure also provides methods and compositions for targeting lysosomal enzymes to lysosomes using a lysosomal targeting peptide that has reduced or diminished binding affinity for the IGF-I receptor and/or reduced or diminished binding affinity for the insulin receptor, and/or is resistant to furin cleavage. The present disclosure also provides targeted lysosomal enzyme fusion proteins comprising a lysosomal enzyme and IGF-II and spacer peptides that provide for improved production and uptake into lysosomes of the lysosomal enzyme fusion protein. Exemplary lysosomal enzymes useful for incorporation into the therapeutic fusion proteins of the present disclosure and the associated diseases to be treated with those fusion proteins are set out in Table 1 below. In certain preferred embodiments, the lysosomal enzyme is a mature human alpha-N-acetylglucosaminidase (Naglu) enzyme and the lysosomal storage disorder is Mucopolysaccharidosis Type IIIB (MPS IIIB; Sanfilippo B Syndrome).

In one aspect, the therapeutic fusion protein of the present disclosure comprises a functional α-N-acetylglucosaminidase enzyme that exhibits detectable enzyme activity and has an amino acid sequence that is at least 90%, 91%, 92%, 93%, 94%, 95%, 96%, 97%, 98%, 99% or 100% identical to the amino acid sequence of the mature human Naglu protein shown in FIG. 1 (SEQ ID NO:1). In another aspect, the disclosure is directed to a fragment of the mature human Naglu protein shown in FIG. 1 (SEQ ID NO:1) that retains detectable Naglu enzyme activity.

In another aspect, the therapeutic fusion protein of the present disclosure comprises a peptide tag having an amino acid sequence at least 90%, 91%, 92%, 93%, 94%, 95%, 96%, 97%, 98%, 99% or 100% identical to the amino acid sequence of amino acids 8-67 of mature human IGF-II. In this regard, amino acids 8-67 of mature human IGF-II has the following amino acid sequence:

(SEQ ID NO: 2)
LCGGELVDTLQFVCGDRGFYFSRPASRVSRRSRGIVEECCFRSCDLALLET
YCATPAKSE.

In various embodiments, the targeted therapeutic fusion protein of the present disclosure comprises a peptide tag having an amino acid sequence at least 90%, 91%, 92%, 93%, 94%, 95%, 96%, 97%, 98%, 99% or 100% identical to the amino acid sequence of amino acids 8-67 of mature human IGF-II having an alanine for arginine substitution at amino acid position 37. In this particularly preferred embodiment, the peptide tag has the following amino acid sequence: LCGGELVDTLQFVCGDRGFYFSRPASRVS ARSRGIVEECCFRSCDLALLETYCATPAKSE (SEQ ID NO:3). The substitution of alanine for arginine at amino acid position 37 has previously been reported to abolish at least one furin protease cleavage site (see, e.g., U.S. Pat. No. 8,563,691).

In another aspect, the therapeutic fusion protein of the present disclosure comprises a spacer peptide located between and linking the lysosomal enzyme and the peptide tag. In various embodiments, the spacer/linker peptide has an amino acid sequence at least 90%, 91%, 92%, 93%, 94%, 95%, 96%, 97%, 98%, 99% or 100% identical to the amino acid sequence of a 31 amino acid rigid linker peptide having the following amino acid sequence: GAPGGGSPAPAPT-PAPAPTPAPAGGGPSGAP (SEQ ID NO:4). In various embodiments, the spacer peptide is from about 25-37, 26-36, 27-35, 28-34, 29-33 or 30-32 amino acids in length and represents a variant of SEQ ID NO:4 wherein 1, 2, 3, 4, 5 or 6 specific amino acids of SEQ ID NO:4 are substituted, added or deleted.

In yet another aspect, the therapeutic fusion protein of the present disclosure comprises (i) a functional α-N-acetylglucosaminidase enzyme having an amino acid sequence that is at least 90%, 91%, 92%, 93%, 94%, 95%, 96%, 97%, 98%, 99% or 100% identical to the amino acid sequence of the mature human Naglu protein shown in FIG. 1 (SEQ ID NO:1), (ii) a peptide tag having an amino acid sequence at least 90%, 91%, 92%, 93%, 94%, 95%, 96%, 97%, 98%, 99% or 100% identical to the amino acid sequence of SEQ ID NO:3, and (iii) a spacer/linker peptide located between the enzyme and the peptide tag having an amino acid sequence at least 90%, 91%, 92%, 93%, 94%, 95%, 96%, 97%, 98%, 99% or 100% identical to the amino acid sequence of the 31 amino acid rigid linker peptide shown herein as SEQ ID NO:4. In one embodiment (herein referred to as BMN001), the therapeutic fusion protein of the present disclosure comprises (i) a functional mature human α-N-acetylglucosaminidase (Naglu) enzyme having the amino acid sequence shown in FIG. 1 (SEQ ID NO:1), (ii) a spacer/linker peptide having the amino acid sequence shown herein as SEQ ID NO:4, and (iii) an IGF-II peptide tag having the amino acid sequence of SEQ ID NO:3. The complete amino acid sequence of the BMN001 therapeutic fusion protein is shown in FIG. 2 (SEQ ID NO:5).

In yet another aspect, the disclosure provides pharmaceutical compositions useful for treating a lysosomal storage disorder in a mammal, wherein said compositions comprise a therapeutic fusion protein of the present disclosure. In various embodiments, the pharmaceutical composition is a formulation that comprises (a) a fusion protein comprising a lysosomal enzyme or functional fragment thereof, a peptide tag having at least 90% sequence identity to SEQ ID NO:2, and a spacer peptide located between said lysosomal enzyme or functional fragment thereof and said peptide tag, said spacer peptide having at least 90% sequence identity to SEQ ID NO:4; and (b) one or more components selected from the group consisting of a buffering agent, an isotonicity agent and an electrolyte agent. The formulations of the present disclosure may be liquid formulations, lyophilized formulations or liquid formulations that were reconstituted from previously lyophilized formulations. In various embodiments, the formulations of the present disclosure are stable.

In various embodiments, the formulations or compositions of matter of the present disclosure may comprise a lysosomal enzyme or functional fragment thereof that comprises the amino acid sequence of SEQ ID NO:1. The formulations of the present disclosure may comprise a fusion protein that comprises or consists of the amino acid sequence of SEQ ID NO:5.

The formulations of the present disclosure may comprise a fusion protein comprising the amino acid sequence of SEQ ID NO:5, a buffering agent, an isotonicity agent, an electrolyte agent, and an anti-adsorption agent. In various embodiments, the formulations of the present disclosure comprise a fusion protein comprising the amino acid sequence of SEQ ID NO:5, sodium phosphate dibasic heptahydrate, sodium phosphate monobasic monohydrate, sodium chloride, and trehalose. In one embodiment, the formulations of the present disclosure comprise a fusion protein comprising the amino acid sequence of SEQ ID NO:5 at a concentration of from about 25 mg/ml to about 35 mg/ml, sodium phosphate dibasic heptahydrate at a concentration of from about 0.15 mg/ml to about 0.25 mg/ml, sodium phosphate monobasic monohydrate at a concentration of from about 0.03 mg/ml to about 0.05 mg/ml, sodium chloride at a concentration of from about 0.8 mg/ml to about 1 mg/ml, and trehalose is at a concentration of from about 7% to about 9%, said formulation having a pH in the range of about 6.5 to about 7.5. In various embodiments, a formulation of the present disclosure comprises a fusion protein comprising the amino acid sequence of SEQ ID NO:5 at a concentration of about 30 mg/ml, sodium phosphate dibasic heptahydrate at a concentration of about 0.19 mg/ml, sodium phosphate monobasic monohydrate at a concentration of about 0.04 mg/ml, sodium chloride at a concentration of about 0.88 mg/ml, and the trehalose concentration at about 8%, said formulation having a pH of about 7.0. These formulations may be in either aqueous or dry/lyophilized form.

In other embodiments, the formulations of the present disclosure comprise a fusion protein comprising the amino acid sequence of SEQ ID NO:5, sodium phosphate dibasic heptahydrate, sodium phosphate monobasic monohydrate, sodium chloride, trehalose, and polysorbate 20. In one embodiment, the formulations of the present disclosure comprise a fusion protein comprising the amino acid sequence of SEQ ID NO:5 at a concentration of from about 25 mg/ml to about 35 mg/ml, sodium phosphate dibasic heptahydrate at a concentration of from about 0.15 mg/ml to about 0.25 mg/ml, sodium phosphate monobasic monohydrate at a concentration of from about 0.03 mg/ml to about 0.05 mg/ml, sodium chloride at a concentration of from about 4.5 mg/ml to about 5.5 mg/ml, trehalose is at a concentration of from about 3% to about 5%, and the polysorbate 20 is at a concentration from about 0.0025% to about 0.0075%, said formulation having a pH in the range of about 6.5 to about 7.5. In various embodiments, a formulation of the present disclosure comprises a fusion protein comprising the amino acid sequence of SEQ ID NO:5 at a concentration of about 30 mg/ml, sodium phosphate dibasic heptahydrate at a concentration of about 0.19 mg/ml, sodium phosphate monobasic monohydrate at a concentration of about 0.04 mg/ml, sodium chloride at a concentration of about 5 mg/ml, the trehalose concentration at about 4%, and the polysorbate 20 concentration at about 0.005% said formulation having a pH of about 7.0. These formulations may be in either aqueous or dry/lyophilized form.

In various embodiments, the formulations of the disclosure comprise sodium phosphate dibasic heptahydrate, sodium phosphate monobasic monohydrate, sodium chloride, potassium chloride, magnesium chloride hexahydrate and calcium chloride dehydrate, and wherein the fusion protein comprises the amino acid sequence of SEQ ID NO:5. In yet other embodiments, the formulations of the present disclosure comprise a fusion protein comprising the amino acid sequence of SEQ ID NO:5 at a concentration of from about 25 mg/ml to about 35 mg/ml, sodium phosphate dibasic heptahydrate at a concentration of from about 0.15 mg/ml to about 0.25 mg/ml, sodium phosphate monobasic monohydrate at a concentration of from about 0.03 mg/ml to about 0.05 mg/ml, sodium chloride at a concentration of from about 8 mg/ml to about 9 mg/ml, potassium chloride at a concentration of from about 0.15 mg/ml to about 0.3 mg/ml, magnesium chloride hexahydrate at a concentration of from about 0.1 mg/ml to about 0.2 mg/ml and calcium chloride dihydrate at a concentration of from about 0.15 mg/ml to about 0.3 mg/ml, said formulation having a pH in the range of about 6.5 to about 7.5. In various embodiments, a formulation of the present disclosure comprises a fusion protein comprising the amino acid sequence of SEQ ID NO:5 at a concentration of about 30 mg/ml, sodium phosphate dibasic heptahydrate at a concentration of about 0.19 mg/ml, sodium phosphate monobasic monohydrate at a concentration of about 0.04 mg/ml, sodium chloride at a concentration of about 8.66 mg/ml, potassium chloride at a concentration of about 0.22 mg/ml, magnesium chloride hexahydrate at a concentration of about 0.16 mg/ml and calcium chloride dihydrate at a concentration of about 0.21 mg/ml, said formulation having a pH of about 7.0. These formulations may be in either aqueous or dry/lyophilized form.

In yet other aspects, the present disclosure is directed to methods for treating lysosomal storage diseases in subjects suffering therefrom, wherein those methods comprise the step of administering a composition of matter or formulation described herein. In various embodiments, the present disclosure is directed to a method of treating MPS IIIB disease in a subject suffering therefrom, wherein the method comprises the step of administering a therapeutic fusion protein having Naglu enzyme activity, or a formulation comprising the same, as described herein. In certain embodiments, the formulation is administered intrathecally, intracerebroventricularly or directly to the CSF via lumbar puncture, which may be either non-volumetric or isovolumetric. Administration of a therapeutic formulation of the present disclosure may occur over a period of from about 5 minutes to about 240 minutes or more, or from about 5 minutes to about 10 minutes. In certain embodiments, administration of a formulation for the treatment of MPS IIIB may occur weekly for a period of at least 24 weeks, preferably at least 48 weeks. In one embodiment, administration of a therapeutically effective amount of a therapeutic fusion protein or formulation of the present disclosure results in reduced severity, intensity or frequency, or delayed onset of at least one symptom or feature of MPS IIIB disease.

In yet other aspects, the present disclosure is directed to a method for slowing the rate of decline, or preventing decline, of at least one symptom of MPS IIIB disease in a subject suffering therefrom, wherein the method comprises the step of administering to the subject a therapeutic fusion protein having Naglu activity or a formulation comprising the same. In various embodiments, the formulation is administered intracerebroventricularly, wherein the intracerebroventricular administration is isovolumetric. Administration of a therapeutic formulation of the present disclosure may occur over a period of from about 5 minutes to about 240 minutes or more, or from about 5 minutes to about 10 minutes. In certain embodiments, administration of a formulation for the treatment of MPS IIIB may occur weekly for a period of at least 24 weeks, preferably at least 48 weeks. These methods may result in improvement of at least one symptom of MPS IIIB disease. In various embodiments, the at least one symptom of MPS IIIB disease can be selected from the group consisting of cognitive decline, decline in language function, decline in motor function, decline in social-emotional function, decline in adaptive function, decline in conceptual thinking, decline in facial recognition, decline in story completion capability, decline in hand function/dexterity, hearing loss, hyperactivity, aggressiveness, or sleep disturbances.

In various aspects, the reduction in the rate of decline, or prevention of decline, of said at least one symptom may be determined by: (a) determining the rate of decline of said symptom prior to said administration, and (b) determining the rate of decline of said symptom subsequent to said administration; wherein a lower rate of decline of said symptom subsequent to said administration as compared to prior to said administration is indicative of a reduction in said rate of decline. These methods may further comprise the steps of determining a development quotient (DQ) for said subject prior to said administration and determining a DQ for said subject subsequent to said administration, wherein a higher DQ for said subject subsequent to said administration as compared to prior to said administration is indicative of a reduction in said rate of decline. In various embodiments, therefore, the present disclosure is directed to methods for stabilizing or reducing the decline of a DQ quotient in a subject suffering from MPS IIIB disease, wherein the methods comprise administering to the subject a therapeutic fusion protein or formulation comprising the same. Development quotients may be determined using the BSID-III or KABC-II tool as described herein and known in the art.

In yet other aspects, the present disclosure is directed to slowing the rate of decline of a cognitive function in a subject suffering from MPS IIIB disease, wherein the method comprises the step of administering to said subject a therapeutically effective amount of a therapeutic fusion protein of the present disclosure, or a formulation thereof, as described herein. In certain embodiments, the fusion protein or formulation thereof may be administered IT, ICV or via lumbar puncture, wherein the administration may be isovolumetric. Administration of a therapeutic formulation of the present disclosure may occur over a period of from about 5 minutes to about 240 minutes or more, or from about 5 minutes to about 10 minutes. In various embodiments, administration of a formulation for the treatment of MPS IIIB may occur weekly for a period of at least 24 weeks, or for at least 48 weeks.

In yet other aspects, the present disclosure is directed to methods for reducing or preventing GAG storage in one or more tissues of the CNS of a subject suffering from a lysosomal storage disorder, wherein the methods comprise administering a therapeutically effective amount of a therapeutic fusion protein or formulation described herein. In one embodiment, the GAG is heparan sulfate and the lysosomal storage disorder is MPS IIIB. As described herein, the administration may be intracerebroventricular, which may be isovolumetric. In various embodiments, GAG storage is reduced in the lysosomes of cells of one or more tissues of the CNS including, for example, gray matter, white matter, periventricular areas, meninges, pia-arachnoid, deep tissues in the cerebral cortex, neocortex, cerebellum, caudate/putamen region, molecular layer, deep regions of the pons or medulla, midbrain, or combinations of two or more of the above.

In various embodiments, the therapeutic fusion protein is delivered to neurons, glial cells, perivascular cells, meningeal cells, and/or neurons of the spinal cord. In certain embodiments, administration of the therapeutic fusion protein or formulation comprising the same results in reduction of GAG storage in one or more of the brain target tissues or spinal cord neurons by at least 10%, 20%, 30%, 40%, 50%, 60%, 70%, 80%, 90%, 1-fold, 1.5-fold or 2-fold or more as compared to an appropriate control (e.g., the pre-treatment GAG storage in the subject).

Other features, objects, and advantages of the present disclosure are apparent in the detailed description that follows. It should be understood, however, that the detailed description, while indicating embodiments of the present disclosure, is given by way of illustration only, not limitation. Various changes and modifications within the scope of the disclosure will become apparent to those skilled in the art from the detailed description.

BRIEF DESCRIPTION OF THE DRAWINGS

FIG. 1 depicts the amino acid sequence (SEQ ID NO:1) of the mature human Naglu protein.

FIG. 2 depicts the amino acid sequence (SEQ ID NO:5) of the BMN001 therapeutic fusion protein.

FIG. 3 is a set of graphs showing Heparan Sulfate (HS) levels in central nervous system tissue (CNS) (upper graph) and cerebrospinal fluid (CSF) (lower graph) in control heterozygous Naglu dogs and homozygous Naglu null affected MPS IIIB dogs treated with vehicle, 12 mg BMN001, or 48 mg BMN001. The data demonstrates that BMN001 reduced HS levels in MPS IIIB dogs to those seen in unaffected heterozygous carrier dogs.

FIG. 10 is a set of graphs showing the reduction of HS and NRE in the CSF of two subjects treated with BMN001.

DEFINITIONS

Figure 4:
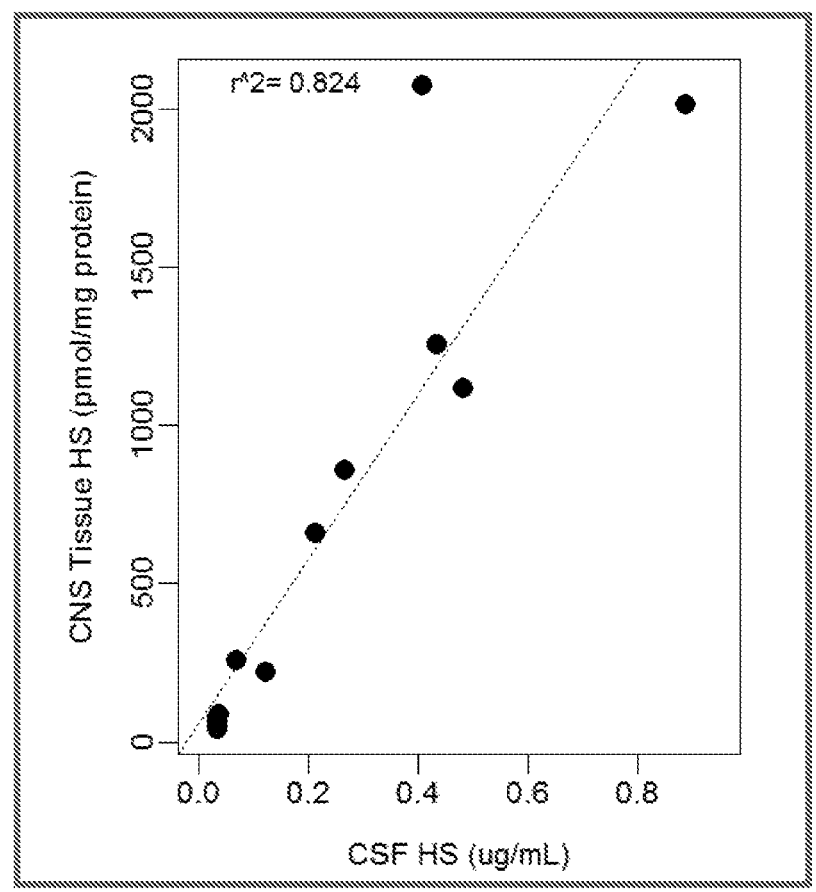
FIG. 4 is a plot of CNS HS levels compared to CSF HS levels showing a strong correlation ($r^2$=0.824) between HS levels in these two compartments.

As used herein, "lysosomal storage diseases" refer to a group of genetic disorders that result from deficiency in at least one of the enzymes (e.g., acid hydrolases) that are required to break macromolecules down to peptides, amino acids, monosaccharides, nucleic acids and fatty acids in lysosomes. As a result, individuals suffering from a lysosomal storage disease have accumulated materials in lysosomes. Exemplary lysosomal storage diseases are listed in Table 1.

As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the disclosure include both wild-type or modified lysosomal enzymes and can be produced using recombinant and synthetic methods or purified from nature sources. Exemplary lysosomal enzymes are listed in Table 1, wherein such lysosomal enzymes may be incorporated into the therapeutic fusion proteins described herein.

As used herein, the term "human alpha-N-acetylglucosaminidase" refers to precursor (i.e., containing the native signal peptide sequence) or processed (i.e., lacking the native signal peptide sequence) wild-type form of human alpha-N-acetylglucosaminidase, or a functional fragment or variant thereof, that is capable of reducing glycosaminoglycan (GAG) levels in mammalian lysosomes or that can rescue or ameliorate one or more MPS IIIB (Sanfilippo B Syndrome) symptoms. In one embodiment, a human Naglu enzyme that finds use herein comprises or consists of the amino acid sequence shown in FIG. 1 (SEQ ID NO:1).

As used herein, the term "functional" as it relates to a lysosomal enzyme, a fusion protein comprising a lysosomal enzyme or fragment of either refers to a polypeptide having the capability of being taken up by mammalian lysosomes and having sufficient enzymatic activity to reduce storage material, i.e., glycosaminoglycan (GAG), in the mammalian lysosome.

As used herein, the term "spacer" (also referred to as "linker") refers to a peptide sequence located between two protein moieties in a fusion protein. A spacer is generally designed to be flexible or to interpose a structure, such as an alpha-helix, between the two protein moieties. A spacer can be of variable length, such as, for example, 10-50, 20-40, or 25-35 amino acids in length. Exemplary spacer sequences are disclosed in greater detail in this specification.

As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease (e.g., MPS IIIB (Sanfilippo B Syndrome)) as the individual being treated, who is about the same age as the individual being treated (to ensure that the stages of the disease in the treated individual and the control individual(s) are comparable).

As used herein, the terms "ameliorate", "amelioration", and grammatical equivalents thereof are meant the prevention, reduction or palliation of a state or disease symptom, the stabilization from decline of a state or disease symptom, or the improvement of a state or disease symptom of/in a subject. Amelioration includes, but does not require complete recovery or complete prevention of a disease condition. In some embodiments, amelioration includes reduction of accumulated materials inside lysosomes of relevant lysosomal storage disease tissues.

As used herein, the terms "subject," "individual" or "patient" refer to a human or a non-human mammalian subject. The individual (also referred to as "patient" or "subject") being treated is an individual (fetus, infant, child, adolescent, or adult human) suffering from a lysosomal storage disease, e.g., MPS IIIB (Sanfilippo B Syndrome) (i.e., either infantile-, juvenile-, or adult-onset or severe/classical type or attenuated type MPS IIIB (Sanfilippo B Syndrome)) or having the potential to develop a lysosomal storage disease (e.g., MPS IIIB (Sanfilippo B Syndrome)).

As used herein, the term "therapeutically effective amount" or "effective amount" refers to an amount of a targeted therapeutic fusion protein (or formulation comprising it) which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic fusion protein or associated pharmaceutical composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic fusion protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

As used herein, the term "treatment" (also "treat" or "treating") refers to any administration of a therapeutic fusion protein or pharmaceutical composition comprising said therapeutic fusion protein that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition.

Alternatively or additionally, such treatment may be of a subject who exhibits one or more established signs of the relevant disease, disorder and/or condition. For example, treatment can refer to improvement of cardiac status (e.g., increase of end-diastolic and/or end-systolic volumes, or reduction, amelioration or prevention of the progressive cardiomyopathy that is typically found in, e.g., Pompe disease) or of pulmonary function (e.g., increase in crying vital capacity over baseline capacity, and/or normalization of oxygen desaturation during crying); improvement in neurodevelopment and/or motor skills (e.g., increase in AIMS score); reduction of storage (e.g., glycosaminoglycan (GAG)) levels in tissue of the individual affected by the disease; or any combination of these effects. In some embodiments, treatment includes improvement of GAG clearance, particularly in reduction or prevention of MPS IIIB (Sanfilippo B Syndrome)-associated neuronal symptoms.

A "stable" or "stabilized" protein-containing formulation is one in which the protein component therein essentially retains its physical, functional and/or chemical stability upon storage over time. Stability can be measured at a selected temperature for a selected time period. Preferably, the formulation is stable at room temperature (about 30° C.) or at 40° C. for at least 1, 3, 6 or 12 months or more, stable at about 2-8° C. for at least 1, 3, 6, 12, 18, 24, 30, 36, 42 or 48 months or more, or stable at either −30° C., −40° C. or −60° C. for at least 1, 3, 6, 12, 18, 24, 30, 36, 42 or 48 months or more. In one aspect, the extent of protein degradation or aggregation during storage can be used as an indicator of protein stability. Thus, a "stable" formulation may be one wherein less than about 20%, more preferably less than about 10%, and most preferably less than about 5%, 4%, 3%, 2% or 1% of the protein component is present in a non-degraded or non-aggregated form in the formulation. "Stable" formulations retain essentially the same functional or therapeutic characteristics, or same physical and/or chemical integrity of the newly prepared formulation. Various analytical techniques for measuring protein stability are available in the art and are reviewed, for example, in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993).

By "isovolumetric" in relation to intrathecal administration of a pharmaceutical composition to the CSF of a subject is meant that prior to administration of a specified volume of the pharmaceutical composition, approximately the same volume of CSF is removed from the subject, thereby maintaining approximately the same volume of fluid in the CSF compartment of the subject being treated.

As used in this application, the terms "about" and "approximately" are used as equivalents. Any numerals used in this application with or without about/approximately are meant to cover any normal fluctuations appreciated by one of ordinary skill in the relevant art.

DETAILED DESCRIPTION OF THE DISCLOSURE

The present disclosure provides compositions, formulations and methods for efficient lysosomal targeting of therapeutic fusion proteins based on the GILT technology. Among other things, the present disclosure provides methods and compositions for targeting therapeutic lysosomal enzymes to lysosomes using lysosomal targeting peptides for the treatment of lysosomal storage disorders. The present disclosure also provides methods and compositions for targeting lysosomal enzymes to lysosomes using a lysosomal targeting peptide that has reduced or diminished binding affinity for the IGF-I receptor and/or reduced or diminished binding affinity for the insulin receptor, and/or is resistant to furin cleavage. The present disclosure also provides targeted lysosomal enzyme fusion proteins comprising a lysosomal enzyme and IGF-II and spacer peptides that provide for improved production and uptake into lysosomes of the lysosomal enzyme fusion protein. The present disclosure also provides formulations that comprise a targeted lysosomal enzyme fusion protein and use thereof for the treatment or prevention of a lysosomal storage disease.

Various aspects of the disclosure are described in detail in the following sections. The use of sections is not meant to limit the disclosure. Each section can apply to any aspect of the disclosure. In this application, the use of "or" means "and/or" unless stated otherwise.

Lysosomal Enzymes

A lysosomal enzyme suitable for incorporation into the therapeutic fusion proteins or formulations of the disclosure includes any enzyme that is capable of reducing accumulated materials in mammalian lysosomes or that can rescue or ameliorate one or more lysosomal storage disease symptoms. Suitable lysosomal enzymes include both wild-type or modified lysosomal enzymes (and functional fragments thereof) and can be produced using recombinant or synthetic methods or purified from natural sources. Exemplary lysosomal enzymes are listed in Table 1.

TABLE 1

| Lysosomal Storage Diseases and Associated Lysosomal Storage Diseases | | |
|---|---|---|
| Disease Name | Enzyme Defect | Substance Stored |
| A. Glycogenosis Disorders | | |
| Pompe Disease | Acid-α1, 4-Glucosidase | Glycogen α1-4 linked oligosaccharides |
| B. Glycolipidosis Disorders | | |
| GM1 Gangliodsidosis | β-Galactosidase | GM1 gangliosides |
| Tay-Sachs Disease | β-Hexosaminidase A | GM2 ganglioside |
| GM2 Gangliosidosis: AB Variant | GM2 Activator Protein | GM2 ganglioside |
| Sandhoff Disease | β-Hexosaminidase A&B | GM2 ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann-Pick, Types A & B | Acid Sphingomyelinase | Sphingomyelin (SM) |
| Niemann-Pick, Type C | Cholesterol Esterification Defect | SM |
| Niemann-Pick, Type D | Unknown | SM |
| Farber Disease | Acid Ceramidase | Ceramide |
| Wolman Disease | Acid Lipase | Cholesteryl esters |
| C. Mucopolysaccharide Disorders | | |
| Hurler Syndrome (MPS IH) | α-L-Iduronidase | Heparan sulfate (HS) & Dermatan sulfate (DS) |
| Scheie Syndrome (MPS IS) | α-L-Iduronidase | HS & DS |
| Hurler-Scheie (MPS IH/S) | α-L-Iduronidase | HS & DS |
| Hunter Syndrome (MPS II) | Iduronate Sulfatase | HS & DS |
| Sanfilippo A (MPS IIIA) | Heparan N-Sulfatase | HS |
| Sanfilippo B (MPS IIIB) | α-N-Acetylglucosaminidase | HS |
| Sanfilippo C (MPS IIIC) | Acetyl-CoA-Glucosaminide Acetyltransferase | HS |
| Sanfilippo D (MPS IIID) | N-Acetylglucosamine-6-Sulfatase | HS |
| Morquio A (MPS IVA) | Galactosamine-6-Sulfatase | Keratan sulfate (KS) |
| Morquio B (MPS IVB) | β-Galactosidase | KS |
| Maroteaux-Lamy (MPS VI) | Arylsulfatase B | DS |
| Sly Syndrome (MPS VII) | β-Glucuronidase | DS, HS & chondroitin sulfate |
| D. Oligosaccharide/Glycoprotein Disorders | | |
| α-Mannosidosis | α-Mannosidase | Mannose/Oligosaccharides |
| β-Mannosidosis | β-Mannosidase | Mannose/Oligosaccharides |
| Fucosidosis | α-L-Fucosidase | Fucosyl Oligosaccharides |
| Aspartylglucosaminuria | N-Aspartyl-β-Glucosaminidase | Aspartylglucosamine Asparagines |
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | Various |
| E. Lysosomal Enzyme Transport Disorders | | |
| Mucolipidosis II (I-Cell Disease) | N-Acetylglucosamine-1-Phosphotransferase | HS |
| Mucolipidosis III (Pseudo-Hurler Polydystrophy) | Same as ML II | HS |
| F. Lysosomal Membrane Transport Disorders | | |
| Cystinosis | Cystine Transport Protein | Free cystine |
| Salla Disease | Sialic Acid Transport Protein | Free sialic acid and glucuronic acid |
| Infantile Sialic Acid Storage Disease | Sialic Acid Transport Protein | Free sialic acid and glucuronic acid |

TABLE 1-continued

Lysosomal Storage Diseases and Associated Lysosomal Storage Diseases

| Disease Name | Enzyme Defect | Substance Stored |
|---|---|---|
| G. Other | | |
| Batten Disease | Unknown | Lipofuscins |
| Infantile Neuronal Ceroid Lipofuscinosis | Palmitoyl-Protein Thioesterase | Lipofuscins |
| Late Infantile Neuronal Ceroid Lipofuscinosis | Tripeptidyl Peptidase I | Lipofuscins |
| Mucolipidosis IV | Unknown | Gangliosides & Hyaluronic Acid |
| Prosaposin | Saposins A, B, C or D | |

In some embodiments, a lysosomal enzyme contemplated herein has an amino acid sequence having from about 90% to about 100%, including 90%, 91%, 92%, 93%, 94%, 95%, 96%, 97%, 98%, 99% and 100%, sequence identity to the naturally-occurring amino acid sequence of a human enzyme shown in Table 1, or the mature form thereof, while still encoding a protein that is functional, i.e., capable of reducing accumulated materials, e.g., GAG, in mammalian lysosomes or that can rescue or ameliorate one or more lysosomal storage disease symptoms. Sequences of the above enzymes are known to those of skill in the art and are available through public databases, such as the National Center for Biotechnology Information maintained by the U.S. National Library of Medicine.

"Percent (%) amino acid sequence identity" with respect to subject and reference amino acid sequences is defined as the percentage of amino acid residues in a subject sequence that are identical with the amino acid residues in the associated reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., Methods in Enzymology 266, 460-480 (1996). WU-BLAST-2 uses several search parameters, most of which are set to the default values. The adjustable parameters are set with the following values: overlap span=1, overlap fraction=0.125, world threshold (T)=11. HSP score (S) and HSP S2 parameters are dynamic values and are established by the program itself, depending upon the composition of the particular sequence, however, the minimum values may be adjusted and are set as indicated above. In other embodiments, % sequence identity between two nucleic acid or amino acid sequences can be determined using the Needle (EMBOSS) or Stretcher (EMBOSS) global sequence alignment tools available at http://www.ebi.ac.uk/Tools/psa/ using the default parameters incorporated therein (incorporated in their entirety by reference herein).

Alpha-N-Acetylglucosaminidase

Alpha-N-acetylglucosaminidase, Naglu, is produced as a precursor molecule that is processed to a mature form. This process generally occurs by removing the 23 amino acid signal peptide as the protein enters the endoplasmic reticulum. Typically, the precursor form is also referred to as full-length precursor or full-length Naglu protein, which contains 743 amino acids. The N-terminal 23 amino acids are cleaved as the precursor protein enters the endoplasmic reticulum, resulting in a processed or mature form. Thus, it is contemplated that the N-terminal 23 amino acids of the native full-length human Naglu protein are generally not required for the Naglu protein activity. The amino acid sequence of the mature form of the human Naglu protein is shown in FIG. 1 and set out in SEQ ID NO:1. The mRNA sequence of human Naglu is described in Genbank Accession number NM 000263. In various embodiments of the present disclosure, the Naglu is human Naglu, with (amino acids 1-743) or without (amino acids 24-743) the associated signal sequence. In a preferred embodiment, the Naglu lysosomal enzyme incorporated in a therapeutic fusion protein has the amino acid sequence shown in FIG. 1 (SEQ ID NO:1). In a particularly preferred embodiment, the Naglu-containing fusion protein has the amino acid sequence shown in FIG. 2 (SEQ ID NO:5). In other embodiments, the fusion protein contains a functional fragment of the mature human Naglu protein, wherein the fragment is generally at least 100, 150, 200, 250, 300, 350, 400, 450, 500, 550, 600, 650 or 700 or more amino acids in length.

Mucopolysaccharidosis III B (Sanfilippo B Syndrome)

One exemplary lysosomal storage disease is Mucopolysaccharidosis III B (MPS IIIB) disease, also known as Sanfilippo Type B Syndrome. MPS IIIB, Sanfilippo B Syndrome, is a rare autosomal recessive genetic disorder that is characterized by a deficiency of the enzyme alpha-N-acetylglucosaminidase (Naglu). In the absence of this enzyme, glycosaminoglycans (GAG), for example the GAG heparan sulfate, and partially degraded GAG molecules cannot be cleared from the body and accumulate in lysosomes of various tissues, resulting in progressive widespread somatic dysfunction (Kakkis et al., *N Engl J Med.* 344(3):182-8 (2001)). It has been shown that GAGs accumulate in lysosomes of neurons and glial cells, with lesser accumulation outside the brain.

Four distinct forms of MPS III, designated MPS IIIA, B, C, and D, have been identified. Each represents a deficiency in one of four enzymes involved in the degradation of the GAG heparan sulfate. All forms include varying degrees of the same clinical symptoms, including coarse facial features, hepatosplenomegaly, corneal clouding and skeletal deformities. Most notably, however, is the severe and progressive loss of cognitive ability, which is tied not only to the accumulation of heparan sulfate in neurons, but also the subsequent elevation of the gangliosides GM2, GM3 and GD2 caused by primary GAG accumulation (Walkley et al., *Ann NY Acad Sci.* 845:188-99 (1998)).

A characteristic clinical feature of Sanfilippo B Syndrome is central nervous system (CNS) degeneration, which results in loss of, or failure to attain, major developmental milestones. The progressive cognitive decline culminates in dementia and premature mortality. The disease typically manifests itself in young children, and the lifespan of an affected individual generally does not extend beyond late teens to early twenties.

MPS III diseases all have similar symptoms that typically manifest in young children. Affected infants are apparently normal, although some mild facial dysmorphism may be noticeable. The stiff joints, hirsuteness and coarse hair typical of other mucopolysaccharidoses are usually not present until late in the disease. After an initial symptom-free interval, patients usually present with a slowing of development and/or behavioral problems, followed by progressive intellectual decline resulting in severe dementia and progressive motor disease. Acquisition of speech is often slow and incomplete. The disease progresses to increasing behavioral disturbance including temper tantrums, hyperactivity, destructiveness, aggressive behavior, pica and sleep disturbance. As affected children have normal muscle strength and mobility, the behavioral disturbances are very difficult to manage. In the final phase of the illness, children become increasingly immobile and unresponsive, often require wheelchairs, and develop swallowing difficulties and seizures. The life-span of an affected child does not usually extend beyond late teens to early twenties.

An alpha-N-acetylglucosaminidase enzyme suitable for treating MPS IIIB (Sanfilippo B Syndrome) includes a wild-type human alpha-N-acetylglucosaminidase, a functional fragment or sequence variant thereof which retains the ability to be taken up into mammalian lysosomes and to hydrolyze alpha, 1,4 linkages at the terminal N-acetyl-D-glucosamine residue in linear oligosaccharides or a targeted therapeutic fusion protein that comprises the wild-type human Naglu enzyme or functional fragment thereof. In particular embodiments, proteins comprising or consisting of the amino acid sequences of SEQ ID NO:1 or SEQ ID NO:5 will find use for the treatment of MPS IIIB.

Efficacy of treatment of MPS IIIB using targeted therapeutic fusion proteins as described herein can be measured using techniques known in the art, as well as by analysis of lysosomal and neuronal biomarkers. Initial experiments are conducted on Naglu knock-out animals (see Li et al., Proc Natl Acad Sci USA 96:14505-510 (1999)). Naglu knockouts present with large amounts of heparan sulfate in the liver and kidney and elevation of gangliosides in the brain.

Assays include analysis of the activity of and biodistribution of the exogenous enzyme, reduction of GAG storage in the lysosomes, particularly in brain cells, and activation of astrocytes and microglia. Levels of various lysosomal or neuronal biomarkers include, but are not limited to, Lysosomal-associated membrane protein 1 (LAMP1), glypican, gangliosides, cholesterol, Subunit c of Mitochondrial ATP Synthase (SCMAS), ubiquitin, P-GSK3b, beta amyloid and P-tau. Survival and behavioral analysis is also performed using techniques known in the field.

In various embodiments, treatment of a lysosomal storage disease refers to decreased lysosomal storage (e.g., of GAG) in various tissues. In various embodiments, treatment refers to decreased lysosomal storage in brain target tissues, spinal cord neurons, and/or peripheral target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to an untreated control subject. In various embodiments, lysosomal storage is decreased by at least 1-fold, 2-fold, 3-fold, 4-fold, 5-fold, 6-fold, 7-fold, 8-fold, 9-fold, 10-fold or more as compared to a control subject.

In various embodiments, treatment refers to increased enzyme activity in various tissues. In various embodiments, treatment refers to increased enzyme activity in brain target tissues, spinal cord neurons and/or peripheral target tissues. In various embodiments, enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900%, 1000% or more as compared to a control. In various embodiments, enzyme activity is increased by at least 1-fold, 2-fold, 3-fold, 4-fold, 5-fold, 6-fold, 7-fold, 8-fold, 9-fold, 10-fold or more as compared to a control. In various embodiments, increased enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In various embodiments, the lysosomal enzyme is Naglu.

Enzyme Replacement Therapy

Enzyme replacement therapy (ERT) is a therapeutic strategy to correct an enzyme deficiency by infusing the missing enzyme into the bloodstream or other body tissue of the patient. As the blood perfuses patient tissues, enzyme is taken up by cells and transported to the lysosome, where the enzyme acts to eliminate material that has accumulated in the lysosomes due to the enzyme deficiency. For lysosomal enzyme replacement therapy to be effective, the therapeutic enzyme must be delivered to lysosomes in the appropriate cells in tissues where the storage defect is manifest. Conventional lysosomal enzyme replacement therapeutics are delivered using carbohydrates naturally attached to the protein to engage specific receptors on the surface of the target cells. One receptor, the cation-independent M6P receptor (CI-MPR), is particularly useful for targeting replacement lysosomal enzymes because the CI-MPR is present on the surface of most cell types.

The terms "cation-independent mannose-6-phosphate receptor (CI-MPR)," "M6P/IGF-II receptor," "CI-MPR/IGF-II receptor," "IGF-II receptor" or "IGF2 Receptor," or abbreviations thereof, are used interchangeably herein, referring to the cellular receptor which binds both M6P and IGF-II.

Glycosylation Independent Lysosomal Targeting

Glycosylation Independent Lysosomal Targeting (GILT) technology was developed to target therapeutic enzymes to lysosomes. Specifically, the GILT technology uses a peptide tag instead of M6P to engage the CI-MPR for lysosomal targeting. Typically, a GILT tag is a protein, peptide, or other moiety that binds the CI-MPR in a mannose-6-phosphate-independent manner. Advantageously, this technology mimics the normal biological mechanism for uptake of lysosomal enzymes, yet does so in a manner independent of mannose-6-phosphate.

A preferred GILT tag is derived from human insulin-like growth factor II (IGF-II). Human IGF-II is a high affinity ligand for the CI-MPR, which is also referred to as IGF-II receptor. Binding of GILT-tagged therapeutic enzymes to the M6P/IGF-II receptor targets the protein to the lysosome via the endocytic pathway. This method has numerous advantages over methods involving glycosylation including simplicity and cost effectiveness, because once the protein is isolated, no further modifications need be made.

Detailed description of the GILT technology and GILT tags can be found in U.S. Application Publication Nos. 2003-0082176, 2004-0006008, 2003-0072761, 2005-0281805, 2005-0244400, U.S. Pat. Nos. 8,492,337 and 8,563,691, and International Publications WO 03/032913, WO 03/032727, WO 02/087510, WO 03/102583, WO 2005/078077, WO 2009/137721 and WO 2014/085621, the disclosures of all of which are hereby incorporated by reference.

In various embodiments, the GILT tag is a furin-resistant GILT tag having the amino acid sequence shown herein as SEQ ID NO:3 (see, e.g., U.S. Pat. No. 8,563,691).

Binding Affinity for the Insulin Receptor

Many IGF-II muteins, including furin-resistant IGF-II muteins, have reduced or diminished binding affinity for the insulin receptor. Thus, in some embodiments, a peptide tag suitable for the disclosure has reduced or diminished binding affinity for the insulin receptor relative to the affinity of naturally-occurring human IGF-II for the insulin receptor. In some embodiments, peptide tags with reduced or diminished binding affinity for the insulin receptor suitable for the disclosure include peptide tags having a binding affinity for the insulin receptor that is more than 1.5-fold, 2-fold, 3-fold, 4-fold, 5-fold, 6-fold, 7-fold, 8-fold, 9-fold, 10-fold, 12-fold, 14-fold, 16-fold, 18-fold, 20-fold, 30-fold, 40-fold, 50-fold, 60-fold, 70-fold, 80-fold, 90-fold, or 100-fold less than that of the wild-type mature human IGF-II. The binding affinity for the insulin receptor can be measured using various in vitro and in vivo assays known in the art.

Administration of Therapeutic Proteins and Formulations

In accordance of the disclosure, a therapeutic fusion protein of the disclosure is typically administered to the individual alone, or in compositions or medicaments comprising the therapeutic protein (e.g., in the manufacture of a medicament for the treatment of the disease), as described herein. The compositions can be formulated with one or more physiologically acceptable carriers or excipients to prepare a pharmaceutical composition. The carriers and compositions can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

The therapeutic protein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

A therapeutic protein (or a composition or medicament containing a therapeutic protein) is administered by any appropriate route. In various embodiments, a therapeutic protein is administered intravenously. In other embodiments, a therapeutic protein is administered by direct administration to a target tissue, such as heart or muscle (e.g., intramuscular), or nervous system (e.g., direct injection into the brain, CNS, CSF; intracerebroventricularly; intrathecally). In various embodiments, a therapeutic protein is administered intrathecally. Methods for the intrathecal administration of therapeutic fusion proteins are known in the art (see, e.g., U.S. Pat. Nos. 7,442,372 and 9,044,473). Alternatively, a therapeutic protein (or a composition or medicament containing a therapeutic protein) can be administered parenterally, transdermally, or transmucosally (e.g., orally or nasally). More than one route can be used concurrently, if desired, e.g., a therapeutic protein is administered intravenously and intrathecally. Concurrent intravenous and intrathecal administration need not be simultaneous, but can be sequential.

A therapeutic protein (or a composition or medicament containing a therapeutic protein) can be administered alone, or in conjunction with other agents, such as antihistamines (e.g., diphenhydramine) or immunosuppressants or other immunotherapeutic agents which counteract anti-GILT-tagged lysosomal enzyme antibodies. The term, "in conjunction with," indicates that the agent is administered prior to, at about the same time as, or following the therapeutic protein (or a composition or medicament containing the therapeutic protein). For example, the agent can be mixed into a composition containing the therapeutic protein, and thereby administered contemporaneously with the therapeutic protein; alternatively, the agent can be administered contemporaneously, without mixing (e.g., by "piggybacking" delivery of the agent on the intravenous line by which the therapeutic protein is also administered, or vice versa). In another example, the agent can be administered separately (e.g., not admixed), but within a short time frame (e.g., within 24 hours) of administration of the therapeutic protein.

The therapeutic protein (or composition or medicament containing the therapeutic protein) is administered in a therapeutically effective amount (i.e., a dosage amount that, when administered at regular intervals, is sufficient to treat the disease, such as by ameliorating symptoms associated with the disease, preventing or delaying the onset of the disease, and/or also lessening the severity or frequency of symptoms of the disease, as described above). The dose which will be therapeutically effective for the treatment of the disease will depend on the nature and extent of the disease's effects, and can be determined by standard clinical techniques. In addition, in vitro or in vivo assays may optionally be employed to help identify optimal dosage ranges using methods known in the art. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems. In various embodiments, the therapeutically effective dosage amount can be, for example, about 0.1-1 mg/kg, about 1-5 mg/kg, about 2.5-20 mg/kg, about 5-20 mg/kg, about 20-50 mg/kg, or about 20-100 mg/kg or about 50-200 mg/kg, or about 2.5 to 20 mg/kg of body weight. The effective dose for a particular individual can be varied (e.g., increased or decreased) over time, depending on the needs of the individual. For example, in times of physical illness or stress, or if disease symptoms worsen, the dosage amount can be increased.

The therapeutically effective amount of the therapeutic protein (or composition or medicament containing the therapeutic protein) is administered at regular intervals, depending on the nature and extent of the disease's effects, and on an ongoing basis.

Administration at an "interval," as used herein, indicates that the therapeutically effective amount is administered periodically (as distinguished from a one-time dose). The interval can be determined by standard clinical techniques. In some embodiments, the therapeutic protein is administered bimonthly, monthly, twice monthly, triweekly, biweekly, weekly, twice weekly, thrice weekly, or daily. The administration interval for a single individual need not be a fixed interval, but can be varied over time, depending on the needs of the individual. For example, in times of physical illness or stress, or if disease symptoms worsen, the interval between doses can be decreased.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

The disclosure additionally pertains to a pharmaceutical composition comprising a therapeutic protein, as described herein, in a container (e.g., a vial, bottle, bag for intravenous administration, syringe, etc.) with a label containing instructions for administration of the composition for treatment of Mucopolysaccharidosis Type IIIB (Sanfilippo B Syndrome), such as by the methods described herein.

In certain embodiments, the present disclosure is directed to formulations comprising a lysosomal enzyme, a targeted therapeutic lysosomal enzyme fusion protein or a functional fragment thereof. In some embodiments, such formulations are liquid formulations, preferably liquid formulations appropriate for intrathecal administration. In other embodiments, the formulation may be a lyophilized formulation or may be a liquid formulation that was reconstituted from a previously lyophilized formulation.

In various embodiments, the formulations of the present disclosure comprise a lysosomal enzyme, a targeted therapeutic lysosomal enzyme fusion protein or a functional fragment thereof in a concentration range of from about 0.1 mg/ml to about 300 mg/ml, or from about 1 mg/ml to about 75 mg/ml, or from about 5 mg/ml to about 50 mg/ml, or from about 10 mg/ml to about 40 mg/ml, or from about 20 mg/ml to about 40 mg/ml, or from about 25 mg/ml to about 35 mg/ml. In certain embodiments, the lysosomal enzyme, fusion protein or fragment thereof may be present at or up to a concentration of about 1, 2, 3, 4, 5, 10, 15, 20, 25, 30, 35, 40, 45, 50, 60, 70, 80, 90, 100, 150, 200, 250 or 300 mg/ml or greater. In various embodiments, the formulations of the present disclosure comprise a lysosomal enzyme, a targeted therapeutic lysosomal enzyme fusion protein or a functional fragment thereof at a concentration of about 30 mg/ml. In various embodiments, the lysosomal enzyme, targeted therapeutic lysosomal enzyme fusion protein or functional fragment thereof has at least about 90%, 91%, 92%, 93%, 94%, 95%, 96%, 97%, 98% or 99% or greater sequence identity to the amino acid sequence shown in FIG. 2 (SEQ ID NO:5). More preferably, the lysosomal enzyme, targeted therapeutic lysosomal enzyme fusion protein or functional fragment thereof is BMN001 having the amino acid sequence shown in FIG. 2 (SEQ ID NO:5).

In further embodiments, the formulations of the present disclosure comprise one or more buffering agents useful for maintaining the pH of the formulation within a desired range. In preferred embodiments, the pH of the liquid formulations of the present disclosure is within the range of from about 5.0 to about 9.0, or from about 5.5 to about 8.5, or from about 6.0 to about 8.0, or from about 6.5 to about 7.5, or from about 6.8 to about 7.2. More preferably, the pH of the liquid formulations of the present disclosure is about 7.0. Various buffering agents and their use in protein-containing formulations are well known in the art and non-limiting examples of buffering agents that find use in the liquid formulations of the present disclosure include, for example, sodium acetate, citric acid monohydrate, sodium citrate dihydrate, sodium phosphate monobasic monohydrate and sodium phosphate dibasic heptahydrate, and the like.

When employed in the formulations of the present disclosure, the concentration of sodium phosphate monobasic monohydrate preferably ranges from about 0.005 mg/ml to about 0.1 mg/ml, or from about 0.01 mg/ml to about 0.1 mg/ml, or from about 0.02 mg/ml to about 0.08 mg/ml, or from about 0.03 mg/ml to about 0.05 mg/ml. In a particularly preferred embodiment, the concentration of sodium phosphate monobasic monohydrate is about 0.04 mg/ml.

When employed in the formulations of the present disclosure, the concentration of sodium phosphate dibasic heptahydrate preferably ranges from about 0.005 mg/ml to about 0.5 mg/ml, or from about 0.01 mg/ml to about 0.5 mg/ml, or from about 0.05 mg/ml to about 0.4 mg/ml, or from about 0.1 mg/ml to about 0.4 mg/ml, or from about 0.15 mg/ml to about 0.25 mg/ml. In a particularly preferred embodiment, the concentration of sodium phosphate dibasic heptahydrate is about 0.19 mg/ml.

In further embodiments, the formulations of the present disclosure comprise one or more isotonicity agents useful for maintaining a desired tonicity and rendering the formulation more compatible for administration, particularly intrathecal administration, to a subject. Various isotonicity agents and their use in protein-containing formulations are well known in the art and non-limiting examples of isotonicity agents that find use in the liquid formulations of the present disclosure include, for example, sodium chloride, trehalose, mannitol, dextrose, glucose, glycerin, sorbitol, xylitol, ethanol, and the like. In particular embodiments, trehalose is used in ranges from about 3% (w/v) to about 10% (w/v), or from about 3% (w/v) to about 5% (w/v) or from about 7% (w/v) to about 9% (w/v). In a preferred embodiment, trehalose is used at about 8% (w/v). In yet another preferred embodiment, trehalose is used at about 4% (w/v).

In various embodiments, the formulations contain an anti-adsorbent agent (e.g., to mitigate adsorption of a protein component to glass or plastic and to reduce the formation of aggregates and multimers). Anti-adsorbent agents include without limitation benzyl alcohol, Polysorbate 20, and Polysorbate 80. In certain embodiments, the anti-adsorbent is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%. In some embodiments the anti-adsorbent agent is Polysorbate 20 in a range from about 0.004% to about 0.006%. In a preferred embodiment, Polysorbate 20 is used at 0.005%.

When employed in the formulations of the present disclosure, the concentration of sodium chloride preferably ranges from about 0.5 mg/ml to about 20 mg/ml, or from about 2 mg/ml to about 15 mg/ml, or from about 5 mg/ml to about 10 mg/ml, or from about 7 mg/ml to about 10 mg/ml, or from about 8 mg/ml to about 9 mg/ml. In a preferred embodiment, the concentration of sodium chloride is about 0.88 mg/ml. In another preferred embodiment, the concentration of sodium chloride is about 5 mg/ml.

In further embodiments, the formulations of the present disclosure comprise one or more electrolyte agents useful for maintaining the level of key electrolyte(s) in the cerebrospinal fluid (CSF) of the subject or for mimicking the natural composition of human CSF. Various electrolyte agents and their use in protein-containing formulations are well known in the art and non-limiting examples of electrolyte agents that find use in the liquid formulations of the present disclosure include, for example, potassium chloride, magnesium chloride, magnesium chloride hexahydrate, calcium chloride, calcium chloride dihydrate, and the like.

When employed in the formulations of the present disclosure, the concentration of potassium chloride preferably ranges from about 0.01 mg/ml to about 1 mg/ml, or from about 0.1 mg/ml to about 0.5 mg/ml, or from about 0.2 mg/ml to about 0.8 mg/ml, or from about 0.15 mg/ml to about 0.4 mg/ml, or from about 0.15 mg/ml to about 0.3 mg/ml. In a preferred embodiment, the concentration of potassium chloride is about 0.22 mg/ml.

When employed in the formulations of the present disclosure, the concentration of magnesium chloride hexahydrate preferably ranges from about 0.01 mg/ml to about 1 mg/ml, or from about 0.1 mg/ml to about 0.8 mg/ml, or from about 0.1 mg/ml to about 0.5 mg/ml, or from about 0.1 mg/ml to about 0.3 mg/ml, or from about 0.1 mg/ml to about 0.2 mg/ml. In a preferred embodiment, the concentration of magnesium chloride hexahydrate is about 0.16 mg/ml.

When employed in the formulations of the present disclosure, the concentration of calcium chloride dihydrate preferably ranges from about 0.01 mg/ml to about 1 mg/ml, or from about 0.1 mg/ml to about 0.8 mg/ml, or from about 0.1 mg/ml to about 0.5 mg/ml, or from about 0.15 mg/ml to about 0.4 mg/ml, or from about 0.15 mg/ml to about 0.3 mg/ml. In a preferred embodiment, the concentration of calcium chloride dihydrate is about 0.21 mg/ml.

In a preferred embodiment, the formulation of the present disclosure is a liquid formulation that comprises the BMN001 targeted therapeutic fusion protein, one or more buffering agents, one or more isotonicity agents and one or more electrolyte agents. More preferably, the liquid formulation comprises BMN001, sodium phosphate dibasic heptahydrate, sodium phosphate monobasic monohydrate, sodium chloride, and trehalose. In one embodiment, the liquid formulation comprises BMN001 at a concentration of from about 25 mg/ml to about 35 mg/ml, sodium phosphate dibasic heptahydrate at a concentration of from about 0.15 to about 0.25 mg/ml, sodium phosphate monobasic monohydrate at a concentration of from about 0.02 mg/ml to about 0.06 mg/ml, sodium chloride at a concentration of from about 0.8 mg/ml to about 1 mg/ml, and trehalose at about 7% (w/v) to about 9% (w/v). In one preferred embodiment, the liquid formulation comprises BMN001 at a concentration of about 30 mg/ml, sodium phosphate dibasic heptahydrate at a concentration of about 0.19 mg/ml, sodium phosphate monobasic monohydrate at a concentration of about 0.04 mg/ml, sodium chloride at a concentration of about 0.88 mg/ml, and trehalose at about 8% (w/v). Preferably, the liquid formulation is at about pH 7.0.

In another preferred embodiment, the formulation of the present disclosure is a liquid formulation that comprises the BMN001 targeted therapeutic fusion protein, one or more buffering agents, one or more isotonicity agents and one or more electrolyte agents. More preferably, the liquid formulation comprises BMN001, sodium phosphate dibasic heptahydrate, sodium phosphate monobasic monohydrate, sodium chloride, trehalose, and polysorbate 20. In one embodiment, the liquid formulation comprises BMN001 at a concentration of from about 25 mg/ml to about 35 mg/ml, sodium phosphate dibasic heptahydrate at a concentration of from about 0.15 to about 0.25 mg/ml, sodium phosphate monobasic monohydrate at a concentration of from about 0.02 mg/ml to about 0.06 mg/ml, sodium chloride at a concentration of from about 4.5 mg/ml to about 5.5 mg/ml, trehalose at about 3% (w/v) to about 5% (w/v), and polysorbate 20 at about 0.004% to about 0.006%. In one preferred embodiment, the liquid formulation comprises BMN001 at a concentration of about 30 mg/ml, sodium phosphate dibasic heptahydrate at a concentration of about 0.19 mg/ml, sodium phosphate monobasic monohydrate at a concentration of about 0.04 mg/ml, sodium chloride at a concentration of about 5 mg/ml, trehalose at about 4% (w/v), and polysorbate 20 at about 0.005%. Preferably, the liquid formulation is at about pH 7.0.

In various embodiments, the formulations may comprise a preservative. Preservatives include, but are not limited to, m-cresol and benzyl alcohol. In certain embodiments, the preservative is in a concentration of about 0.4%±0.2%, or about 1%±0.5%, or about 1.5%±0.5%, or about 2.0%±0.5%. In certain embodiments of the disclosure, the formulation does not contain a preservative.

In various embodiments, the formulations comprise a stabilizer. Non-limiting examples of stabilizers include glycerin, glycerol, thioglycerol, methionine, and ascorbic acid and salts thereof. In some embodiments, when the stabilizer is thioglycerol or ascorbic acid or a salt thereof, the stabilizer is in a concentration from about 0.1% to about 1%. In other embodiments, when the stabilizer is methionine, the stabilizer is in a concentration from about 0.01% to about 0.5%, or from about 0.01% to about 0.2%. In still other embodiments, when the stabilizer is glycerin, the stabilizer is in a concentration from about 5% to about 100% (neat).

In various embodiments, the compositions contain an antioxidant. Exemplary anti-oxidants include without limitation methionine and ascorbic acid. In certain embodiments, the molar ratio of antioxidant to protein is from about 0.1:1 to about 15:1, or from about 1:1 to about 15:1, or from about 0.5:1 to about 10:1, or from about 1:1 to about 10:1 or from about 3:1 to about 10:1.

Pharmaceutically acceptable salts can be used in the formulations, including without limitation mineral acid salts (e.g., hydrochloride, hydrobromide, phosphate, sulfate), salts of organic acids (e.g., acetate, propionate, malonate, benzoate, mesylate, tosylate), and salts of amines (e.g., isopropylamine, trimethylamine, dicyclohexylamine, diethanolamine). A thorough discussion of pharmaceutically acceptable salts is found in Remington's Pharmaceutical Sciences, 18th Edition, Mack Publishing Company, (Easton, Pa. (1990)).

Examples of other formulary additives and compositions useful for intrathecal or ICV delivery are described in WO2013/096899, which is herein incorporated by reference.

The formulations of the present disclosure are stable and can be stored for extended periods of time without an unacceptable change in quality, potency, or purity. In one aspect, the formulation is stable at a temperature of about 5° C. (e.g., 2° C. to 8° C.) for at least 1 month, for example, at least 1 month, at least 3 months, at least 6 months, at least 12 months, at least 18 months, at least 24 months, or more. In another aspect, the formulation is stable at a temperature of less than or equal to about −20° C. for at least 6 months, for example, at least 6 months, at least 12 months, at least 18 months, at least 24 months, at least 36 months, or more. In another aspect, the formulation is stable at a temperature of less than or equal to about −40° C. for at least 6 months, for example, at least 6 months, at least 12 months, at least 18 months, at least 24 months, at least 36 months, or more. In another aspect, the formulation is stable at a temperature of less than or equal to about −60° C. for at least 6 months, for example, at least 6 months, at least 12 months, at least 18 months, at least 24 months, at least 36 months, or more.

Suitable formulations of the present disclosure include, liquid, lyophilized or reconstituted lyophilized formulations. In various aspects, the formulations of the present disclosure are contained within a container, which in one aspect, may comprise a single dosage form of the formulation. Exemplary containers include, for example, ampules, vials, bottles, cartridges, reservoirs and pre-filled syringes.

Intrathecal Administration of the Pharmaceutically Acceptable Formulations

In various embodiments, the enzyme, enzyme fusion protein or formulation comprising the same is administered by direct introduction into the central nervous system of the subject, e.g., into the cerebrospinal fluid of the subject. In certain aspects of the disclosure, the enzyme is introduced intrathecally, e.g., into the lumbar area, or the cisterna magna or intraventricularly (or intracerebroventricularly (ICV)) into a cerebral ventricle space. Methods of administering a lysosomal enzyme or fusion protein comprising a functional lysosomal enzyme intrathecally or intracerebroventricularly are described in U.S. Pat. Nos. 7,442,372, 9,044,473 and 9,089,566, incorporated herein by reference in their entirety.

Those of skill in the art are aware of devices that may be used to effect intrathecal administration of a therapeutic composition. For example, the therapy may be given using an Ommaya reservoir which is in common use for intrathecally administering drugs for meningeal carcinomatosis (Ommaya et al., Lancet 2: 983-84 (1963)). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions to an individual are described in U.S. Pat. No. 6,217,552, incorporated herein by reference. Alternatively, the composition may be intrathecally given, for example, by a single injection, or continuous infusion. It should be understood that the dosage treatment may be in the form of a single dose administration or multiple doses.

As used herein, the term "intrathecal administration" is intended to include delivering a pharmaceutical composition directly into the cerebrospinal fluid of a subject, by techniques including lateral cerebroventricular injection (i.e., intracerebroventricularly) through a burr hole or cisternal or lumbar puncture, or the like (described in Lazorthes et al. *Advances in Drug Delivery Systems and Applications in Neurosurgery,* 143-192 (1991) and Ommaya et al., *Cancer Drug Delivery* 1:169-179 (1984), the contents of which are incorporated herein by reference). The term "lumbar region" is intended to include the area between the third and fourth lumbar (lower back) vertebrae and, more inclusively, the L2-S1 region of the spine.

The term "cisterna magna" is intended to include access to the space around and below the cerebellum via the opening between the skull and the top of the spine. The term "cerebral ventricle" is intended to include the cavities in the brain that are continuous with the central canal of the spinal cord. Administration of a pharmaceutical composition in accordance with the present disclosure to any of the above mentioned sites can be achieved by direct injection of the composition or by the use of infusion pumps. For injection, the composition of the disclosure can be formulated in liquid solutions, preferably in physiologically compatible buffers such as Hank's solution, Ringer's solution or phosphate buffer. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In various embodiments of the disclosure, the enzyme is administered by lateral cerebroventricular injection into the brain of a subject. The injection can be made, for example, through a burr hole made in the subject's skull. In another embodiment, the enzyme fusion protein and/or other pharmaceutical formulation is administered through a surgically inserted shunt into the cerebral ventricle of a subject. For example, the injection can be made into the lateral ventricles, which are larger, even though injection into the third and fourth smaller ventricles can also be made.

In various embodiments, the pharmaceutical compositions used in the present disclosure are administered by injection into the cisterna magna, or lumbar area of a subject. In another embodiment of the method of the disclosure, the pharmaceutically acceptable formulation provides sustained delivery, e.g., "slow release" of the enzyme or other pharmaceutical composition used in the present disclosure, to a subject for at least one, two, three, four weeks or longer periods of time after the pharmaceutically acceptable formulation is administered to the subject.

In various embodiments, a therapeutic fusion protein is delivered to one or more surface or shallow tissues of the brain or spinal cord. For example, in various embodiments, a therapeutic fusion protein is delivered to one or more surface or shallow tissues of the cerebrum or spinal cord. In some embodiments, the targeted surface or shallow tissues of the cerebrum or spinal cord are located within 4 mm from the surface of the cerebrum. In some embodiments, the targeted surface or shallow tissues of the cerebrum are selected from pia mater tissues, cerebral cortical ribbon tissues, hippocampus, Virchow Robin space, blood vessels within the VR space, the hippocampus, portions of the hypothalamus on the inferior surface of the brain, the optic nerves and tracts, the olfactory bulb and projections, and combinations thereof.

In some embodiments, a therapeutic fusion protein is delivered to one or more deep tissues of the cerebrum or spinal cord. In some embodiments, the targeted surface or shallow tissues of the cerebrum or spinal cord are located 4 mm (e.g., 5 mm, 6 mm, 7 mm, 8 mm, 9 mm, or 10 mm) below (or internal to) the surface of the cerebrum. In some embodiments, targeted deep tissues of the cerebrum include the cerebral cortical ribbon. In some embodiments, targeted deep tissues of the cerebrum include one or more of the diencephalon (e.g., the hypothalamus, thalamus, prethalamus, subthalamus, etc.), metencephalon, lentiform nuclei, the basal ganglia, caudate, putamen, amygdala, globus pallidus, and combinations thereof.

In various embodiments, a targeted surface or shallow tissue of the spinal cord contains pia matter and/or the tracts of white matter. In various embodiments, a targeted deep tissue of the spinal cord contains spinal cord grey matter and/or ependymal cells. In some embodiments, a therapeutic fusion protein is delivered to neurons of the spinal cord.

In various embodiments, a therapeutic fusion protein is delivered to one or more tissues of the cerebellum. In certain embodiments, the targeted one or more tissues of the cerebellum are selected from the group consisting of tissues of the molecular layer, tissues of the Purkinje cell layer, tissues of the Granular cell layer, cerebellar peduncles, and combination thereof. In some embodiments, therapeutic agents (e.g., enzymes) are delivered to one or more deep tissues of the cerebellum including, but not limited to, tissues of the Purkinje cell layer, tissues of the Granular cell layer, deep cerebellar white matter tissue (e.g., deep relative to the Granular cell layer), and deep cerebellar nuclei tissue.

In various embodiments, a therapeutic fusion protein is delivered to one or more tissues of the brainstem. In some embodiments, the targeted one or more tissues of the brainstem include brain stem white matter tissue and/or brain stem nuclei tissue.

In various embodiments, a therapeutic fusion protein is delivered to various brain tissues including, but not limited to, gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof.

In various embodiments, a therapeutic fusion protein is delivered to various cells in the brain including, but not limited to, neurons, glial cells, perivascular cells and/or meningeal cells. In some embodiments, a therapeutic protein is delivered to oligodendrocytes of deep white matter.

In certain preferred embodiments, in order to treat MPS IIIB disease in a human subject, reduce the rate of decline of at least one symptom (including cognitive decline) of MPS IIIB in a human subject, or to reduce or prevent GAG storage in one or more tissues of the CNS of a subject suffering from MPS IIIB disease, about 30 mg, 100 mg or 300 mg of therapeutic fusion protein, or from about 30 mg-300 mg, 30 mg-200 mg or 30 mg-100 mg of therapeutic fusion protein, is administered once weekly ICV (isovolumetric) for a time period of at least about 24, preferably 48 weeks.

Kits for Use in the Methods of the Disclosure

The agents utilized in the methods of the disclosure may be provided in a kit, which kit may further include instructions for use. Such a kit will comprise a lysosomal enzyme or fusion protein as described herein comprising an enzyme for use in the treatment of a lysosomal storage disease and a lysosomal targeting moiety, usually in a dose and formulation suitable for administration to the host. In various embodiments, the kit may comprise one or more device(s) for delivering the enzyme intrathecally.

A kit of the present disclosure may comprise instructions for the intrathecal administration of the therapeutic compositions of the present disclosure, in addition to the therapeutic compositions. In certain embodiments, the kits of the disclosure may comprise catheter(s), pump(s), or other devices for the intrathecal administration of the enzyme replacement therapy that are preloaded with the therapeutic compositions of the present disclosure. For example, catheters preloaded with 0.001-0.01 mg, 0.01-0.1 mg, 0.1-1.0 mg, 1.0-10 mg, 10-100 mg, or more of a therapeutic fusion protein comprising a lysosomal enzyme and lysosomal targeting moiety, such as Naglu and an IGF-II peptide tag, in a pharmaceutically acceptable formulation are specifically contemplated. Exemplary catheters may include single use catheters that can be discarded after use.

In certain embodiments, the kits of the present disclosure may comprise one or more of the following components, an extension line (e.g., Smiths Medical PN:536040), an in-line filter (e.g., Smiths Medical PN:FS116), a port needle (e.g., Smiths Medical PN:21-2737-24), a syringe (e.g., Becton Dickinson PN:309604) or a syringe needle (e.g., Becton Dickinson PN:305196).

Methods for Treating Sanfilippo B Syndrome

Intrathecal (e.g., ICV or lumbar) administration of a Naglu enzyme or fusion protein thereof (including BMN001) into the CSF of the patient can be used for the prevention or treatment of one or more symptom or adverse consequence of MPS IIIB disease in humans. In this regard, it is expected that intrathecal administration of a therapeutically effective amount of a Naglu enzyme or fusion protein thereof (including BMN001) will result in improvement of at least one symptom or adverse consequence of MPS IIIB disease, a slowing or reduction of the progression of at least one symptom or adverse consequence of MPS IIIB or a stabilization of decline of at least one symptom or adverse consequence of MPS IIIB. In this regard, known symptoms or adverse consequences of MPS IIIB disease in humans include, for example, detectable decline in one or more of the following: cognitive function, language function, motor function, social-emotional function, adaptive function, conceptual thinking, facial recognition, story completion, pattern reasoning and hand function/dexterity.

In order to quantify the therapeutic effect of an administered enzyme or fusion protein thereof, any of a variety of well-known and routinely employed neurocognitive tests can be employed to derive a developmental quotient (DQ) score. In one embodiment, the DQ score is a cognitive function DQ score.

In one embodiment of the present disclosure, a DQ score for a human subject may be obtained through use of the Bayley Scales of Infant Development, 3rd Edition (BSID-III) (Bayley, *Bayley Scales of Infant and Toddler Development (Bayley-III)*. Technical Manual. Third ed. San Antonio: Psychological Corp., 2006, incorporated herein by reference). The BSID-III is a tool comprised of 5 domains (cognitive, language, motor, social-emotional and adaptive functioning) intended to assess developmental function in children ages 1 to 42 months. In certain embodiments, neither the social-emotional nor adaptive functioning domains of the BSID-III test are used. In one embodiment, only the cognitive domain is used to determine a DQ score.

In certain embodiments, the BSID-III's cognitive domain may be the primary focus of the study. The cognitive scale is administered individually by a qualified examiner and captures the development of critical skills such as processing speed, problem solving and play. Importantly, the cognitive assessments do not require the subject to respond verbally; as a result, this test is particularly useful for assessing cognitive function in conditions such as MPS IIIB where there are problems with expressive language. Raw scores within one domain may be converted to a scaled score, which may then be converted to composite scores encompassing several domains. Mean raw scores associated with different ages also allow for the generation of age-equivalent scores and a DQ.

In certain embodiments, the language and motor domains of the BSID-III may also be administered. The language domain consists of 2 subtests (receptive communication and expressive communication) and the motor domain consists of 2 subtests (fine motor and gross motor).

In another embodiment of the present disclosure, a DQ score for a human subject may be obtained through use of the Kaufman Assessment Battery for Children, 2nd Edition (KABC-II) (Kaufman et al., *Kaufman Assessment Battery for Children*. Second Edition ed. Pearson Assessment, Inc. 2004, incorporated herein by reference). The KABC-II is a clinical instrument (psychological diagnostic test) for assessing cognitive development. Like the BSID, the KABC can be used to generate age-equivalent scores and hence a DQ. Since many parts of the test are non-verbal it is particularly suited for assessing function in children who may have difficulties in both hearing and in verbal communication, both of which are conditions relevant to the MPS IIIB patient population. In addition, the test has been translated into a number of different languages across the world. The subtests that comprise the Kaufman nonverbal index include the following: conceptual thinking, face recognition, story completion, triangles, pattern reasoning, and hand movements. In addition to the nonverbal index subtests, the knowledge cluster subtests (riddles, expressive vocabulary and verbal knowledge) may be administered to subjects who have language.

In certain embodiments, the algorithm employed for determining whether to employ the BSID-III or KABC-II test for determining a DQ quotient is described by Delaney et al., *JIMD Rep.* 13:129-137 (2014).

Results from either the BSID-III tool (or cognitive subtest thereof) or the KABC-II nonverbal index are used to determine the DQ score for subjects either prior to treatment, or during or after treatment, with a therapeutic enzyme or fusion protein thereof. More specifically, using the BSID-III or KABC-II tools described above, the subject is assigned an "age-equivalent rating" (in months) based upon their performance in the tool employed. The DQ score is then calculated by dividing that "age-equivalent rating" by the actual age of the subject (in months), and then multiplying by 100. To illustrate, an MPS IIIB subject having an actual age of 60 months that is assigned an "age-equivalent rating" of 48 months based upon his/her performance in the tool employed, would have a DQ calculated as follows: (48 divided by 60)×100=80. On the other hand, a fully-functioning 60 month old who is assigned an "age-equivalent rating" of 60 months would have a DQ of (60 divided by 60)×100=100. As cognitive function, language function, motor function, social-emotional function, adaptive function, conceptual thinking, facial recognition, story completion, pattern reasoning and/or hand function/dexterity tend to decline over time in human MPS IIIB patients, it is expected that DQ scores for untreated MPS IIIB subjects will decline over time. It is the intention of the present disclosure to reduce the observed decline in DQ, stabilize DQ over time or improve DQ over time through administration of a therapeutic protein described herein. The beneficial effect of administration of a therapeutic fusion protein of the present disclosure, or formulation comprising the same, can be detected by determining a DQ score for a subject prior to treatment and comparing to a DQ score for a subject after treatment.

The disclosure will be further and more specifically described by the following examples. Examples, however, are included for illustration purposes, not for limitation.

Example 1—Formulation Development

Lysosomal enzyme fusions proteins (including mature human alpha-N-acetylglucosaminidase [Naglu] fusion proteins) comprising GILT tags and spacers have been disclosed in U.S. Patent Publication Nos. 2003-0082176, 2004-0006008, 2003-0072761, 2004-0005309, 2005-0281805, 2005-0244400, U.S. Pat. Nos. 8,492,337 and 8,563,691, and International Publications WO 03/032913, WO 03/032727, WO 02/087510, WO 03/102583, WO 2005/078077, WO 2009/137721 and WO 2014/085621, the disclosures of which are all incorporated herein by reference.

In one particularly preferred embodiment (referred to herein as BMN001), a Naglu/IGF-II fusion protein comprising a functional mature human Naglu enzyme fused through a rigid linker to a furin-resistant IFG-II peptide consisting of amino acids 8-67 of the mature human IGF-II and having an alanine for arginine substitution at amino acid position 37 thereof was prepared and formulated for use in in vivo safety and efficacy studies. The peptide linker employed in BMN001 has the amino acid sequence shown herein as SEQ ID NO:4. The complete amino acid sequence of the BMN001 therapeutic fusion protein is shown in FIG. 2 (SEQ ID NO:5).

In order to identify excipients and associated formulary conditions that would be amenable for a BMN001 liquid formulation appropriate for human clinical use via intrathecal administration, various experiments were conducted. First, the propensity of BMN001 to aggregate in liquid formulation at various pH's was tested as follows. Initially, BMN001 was introduced into a liquid formulation comprising a citrate buffer at pH 5.0 or 6.5, or an artificial human CSF liquid formulation at pH 6.0, 6.5, 7.0 and 8.0, and static light scattering analyses were conducted to measure the propensity of BMN001 to aggregate at different pH and increasing temperature. The results of these analyses demonstrated that BMN001 tends to aggregate more readily with increasing temperature at lower pH (pH 5.0 to 6.0), than it does at higher, more neutral pH (about pH 7.0). Moreover, SEC analyses performed on BMN001 liquid formulations at 25° C. and varying pH demonstrated a significantly higher percentage of aggregated, multimeric BMN001 at pH's below 6.5, as compared to less acidic, more neutral pH's in the range of from about 6.5 to about pH 7.5. Finally, SEC analyses performed on BMN001 liquid formulations at varying pH subjected to 10 cycles of freeze/thaw demonstrated a significantly higher percentage of aggregated, multimeric BMN001 at pH's below 6.5, as compared to less acidic, more neutral pH's in the range of about 7.0. These combined data suggest the use of a pH in the range of from about 6.5 to about 7.5, preferably about 7.0, would be beneficial for a clinical BMN001 liquid formulation.

Next, liquid formulations comprising varying concentrations of BMN001 were tested to determine the effect of fusion protein concentration on aggregate/multimer formation during 5 cycles of freeze/thaw. In these experiments, liquid formulations containing 1, 5, 15 or 24 mg/ml of BMN001 were prepared at pH 5.0, 6.0, 7.0 and 8.0. After five cycles of freeze/thaw, the relative percentage of aggregate/multimer to monomer tended to be larger in the lower protein concentration formulations than in the formulations comprising a larger concentration of fusion protein. Moreover, aggregate/multimer formation tended to occur more frequently at more acidic pH than at a neutral pH. Addition of 2% trehalose prevented fusion protein aggregation when compared to the same formulation in the absence of trehalose. These results suggest that liquid formulations comprising at least about 24 mg/ml of BMN001 fusion protein are preferable to formulations comprising a lower fusion protein concentration. These surprising results demonstrating that liquid formulations having higher protein concentration (i.e., approximately 30 mg/ml) tend to have lower relative percentage of aggregate/multimer formation provides significant benefit for intrathecal administration to humans, where such administration is quite sensitive to the total volume of fluid being administered. As such, the formulations of the present disclosure, including BMN001-containing formulations, having a protein concentration of at least 24 mg/ml, including those formulations having a protein concentration of about 30 mg/ml, are quite useful for intrathecal administration to human subjects.

Next, a variety of formulary excipients were screened for their ability to prevent agitation- or freeze/thaw-induced aggregate formation of BMN001 as measured by static light scattering analysis. Liquid formulations comprising identical amounts of BMN001 were prepared that comprised either (i) 180 mM N-acetylglucosamine, (ii) 222 mM glucose, (iii) 234 mM sucrose, (iv) 212 mM trehalose, (v) 220 mM sorbitol, (vi) 200 mM glutamic acid, (vii) 200 mM glutamine, (viii) 200 mM arginine, (ix) 200 mM histidine, (x) 200 mM glycine, (xi) 0.1% w/v polysorbate 20, or (xii) 0.1% w/v poloaxamer 188. The results of these analyses demonstrated that addition of one or more amino acids tended to destabilize the liquid formulation as evidenced by increased aggregate/multimer formation as induced by either agitation or freeze/thaw. On the other hand, addition of one or more sugar/polyol tended to reduce the relative amount of aggregate/multimer formed as induced by either agitation or freeze/thaw.

Based upon the formulation development work described above and additional experimentation not described herein, a final BMN001 liquid formulation was developed for use in further human clinical development as described below. The BMN001 clinical formulation employed in the human clinical studies described in Example 3 below consisted of the following components: (i) 30 mg/ml BMN001 fusion protein, (ii) 0.19 mg/ml sodium phosphate dibasic, heptahydrate, (iii) 0.04 mg/ml sodium phosphate monobasic monohydrate, (iv) 8.66 mg/ml sodium chloride, (v) 0.22 mg/ml potassium chloride, (vi) 0.16 mg/ml magnesium chloride, hexahydrate, and (vi) 0.21 mg/ml calcium chloride dihydrate. This BMN001 clinical formulation was formulated at a final pH of 7.0. The BMN001 clinical formulation may be packaged in a clear borosilicate glass vial closed with a fluoropolymer-coated bromobutyl rubber stopper, capped with an aluminum seal and stored frozen at about −40° C. until thawed for use.

Example 2—BMN001 for the Treatment of Sanfilippo B Syndrome (Pre-Clinical Studies)

Nonclinical studies were conducted as described herein and indicate likely therapeutic benefit without significant risk of BMN001-related toxicity for human patients with MPS IIIB disease.

The nonclinical studies described herein were designed to support chronic ICV infusion of BMN001 for the treatment of MPS IIIB in human patients. The primary pharmacodynamics (PD), cardiovascular (CV) and CNS safety pharmacology, PK, CNS distribution and toxicity of BMN001 administered by the ICV route have been characterized in one single dose study in normal animals (cynomolgus monkey) and four repeat dose studies in normal and disease models of MPS IIIB (Naglu-knockout [KO] mouse, WT and NAGLU-null dog (Ellinwood et al., *J. Inherit. Metab. Dis.* 26(5):489-504 (2003) and cynomolgus monkey). These species were selected due to the high degree of NAGLU amino acid sequence homology, CI-MPR expression and amino acid sequence identity. The animal models of disease also display some of the key features of the human MPS IIIB disease, including accumulation of lysosomal storage material, neuron death, decline in function and reduced lifespan with similar relative timing of disease progression. They also display certain neurologic signs, including tremors and ataxia, which can be used to functionally track the underlying CNS pathology and potentially be used to monitor response to treatment. Therefore, these models provide valuable insight as to pharmacological attenuation of disease progression using clinically translatable endpoints.

Primary PD assessments for BMN001 were conducted in IGF2 receptor binding assays, MPS IIIB human fibroblasts and the two available animal models of MPS IIIB, the NAGLU knockout (KO) mouse and juvenile NAGLU-null dog and demonstrate the robust pharmacological activity of BMN001. Analysis of IGF2 receptor binding of BMN001 lots used in these studies resulted in a calculated average $IC_{50}$ of 0.28 nM. The in vitro cellular uptake of BMN001 and cellular half-life was determined in MPS IIIB human fibroblasts. The lysosomal $K_{uptake}$ of BMN001 was defined as the concentration at which uptake into the lysosome is at half the maximal rate and was 3.7-6.4 nM (5.3 nM average) with a lysosomal half-life of approximately 9.5 days.

In the MPS IIIB mouse disease model, ICV administration of BMN001 reversed the pathology of the disease. Repeat-dose studies in these mice show consistent tissue distribution of BMN001 across the CNS. The primary PD assessment demonstrated the effects of BMN001 on both biochemical and histological endpoints. ICV administration of BMN001 to Naglu-KO mice resulted in reduction of lysosomal storage material accumulation (i.e., GAG/heparan sulfate accumulation) with accompanying improvement in histological and immune-histological indices of lysosomal function. More specifically, when evaluated 24 hours after the final dose of BMN001, treatment resulted in a marked increase of Naglu enzyme activity and a concomitant decrease in beta-hexosaminidase activity and levels of total heparan sulfate and LAMP-2. Naglu activity was detectable in brain tissues, not only in cortex, hippocampus, dentate gyrus and thalamus, but also in remote distal geographic locations including amygdyla, perirhinal cortex and hypothalamus. Significant decreases in the levels of CD68, SCMAS, beta-amyloid, p-Tau, P-GSK3beta and glypican 5 were also observed. Levels of heparan sulfate, Naglu-specific NREs and beta-hexosaminidase activity continued to decrease over the 7, 14 and 28 day post-last-dose time points.

In NAGLU-null dogs, the PD effects of BMN001 observed after 6 months of ICV administration included reduction of cerebrospinal fluid (CSF) lysosomal storage material and maintenance of motor function. Additional pharmacodynamics endpoints, including cognition and delay in disease progression, are currently being assessed as follows. Six independent groups having 4 previously immunotolerized dogs per group were treated biweekly by ICV infusion between ages 4 and 18 months as follows:

Group 1 (normal NAGLU+dogs)—ICV vehicle only (10 ml/kg);
Group 2 (normal NAGLU+dogs)—BMN001 (12 mg/kg);
Group 3 (normal NAGLU+dogs)—BMN001 (12 mg/kg, escalated to 48 mg/kg at dose 3);
Group 4 (NAGLU–null dogs)—ICV vehicle only (10 ml/kg);
Group 5 (NAGLU–null dogs)—BMN001 (12 mg/kg);
Group 6 (NAGLU–null dogs)—BMN001 (12 mg/kg, escalated to 48 mg/kg at dose 3).

Heparan Sulfate (HS) levels were measured in the CNS tissue, CSF, and cerebellum tissue in the dogs from groups 1, 4, 5, and 6. As shown in FIG. 3, BMN001 reduced HS levels in both CNS tissue and in the CSF in MPS IIIB dogs in a dose dependent fashion, with the 48 mg/kg dose reducing HS to wild-type levels. The levels of HS in the CNS and CSF in each group of dogs was evaluated and compared. As shown in FIG. 4, there is a strong correlation in the HS levels in these two brain compartments, demonstrating BMN001's ability to reduce HS uniformly throughout the brain.

Figure 5:
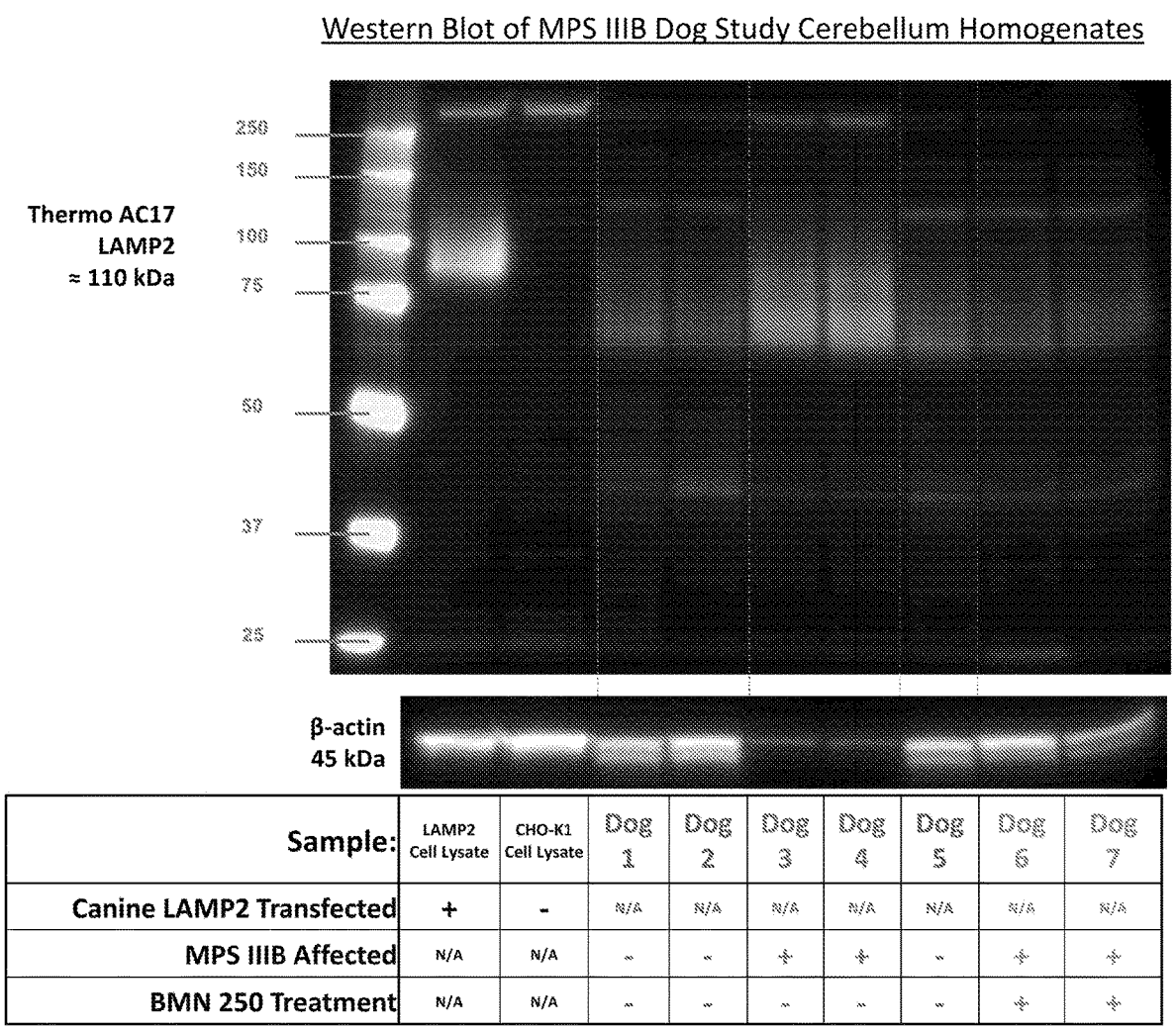
FIG. 5 is a western blot of canine cerebellum from wild-type dogs, untreated MPS IIIB dogs, and BMN001 treated MPS IIIB dogs probed with an antibody specific for canine LAMP2 protein, showing that LAMP2 levels are elevated in untreated MPS IIIB dogs relative to wild-type and that treatment with BMN001 reduces LAMP2 to wild-type levels in treated MPS IIIB dogs.

The effect of BMN001 treatment on LAMP2 levels was also investigated. Cerebellum tissue homogenate samples (18 μg protein/lane) from wild-type, untreated MPSIIIB-affected dogs, and MPSIIIB-affected dogs treated with BMN001 were electrophoresed and blotted under non-reducing conditions, then probed with unlabeled AC17 and detected with an HRP-conjugated anti-mouse IgG secondary antibody. LAMP2-expressing or control CHO-K1 cell lysates were included in the blots as controls (5 μg protein/lane). To assess the total amount of protein loaded into each lane, cerebellum homogenate blots were stripped and re-probed for β-actin. As shown in FIG. 5, untreated MPSIIIB-affected dogs had high levels of LAMP2 relative to wild-type dogs. However, treatment with BMN001 reduced the LAMP2 levels in MPSIIIB-affected dogs to levels seen in wild-type dogs.

Figure 6:
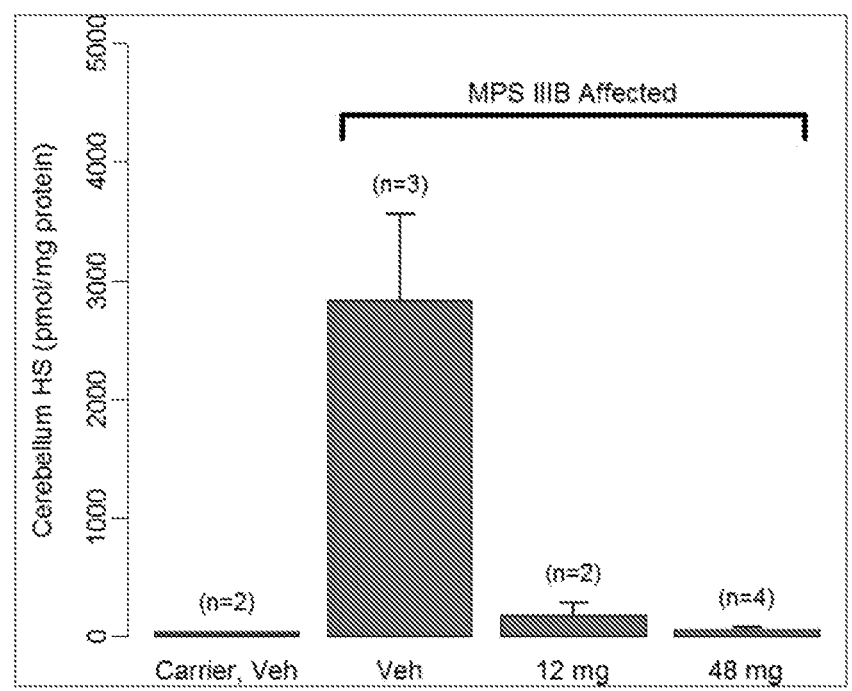
FIG. 6 is a graph showing Heparan Sulfate (HS) levels in cerebellum in control heterozygous Naglu dogs and homozygous Naglu null affected MPS IIIB dogs treated with vehicle, 12 mg BMN001, or 48 mg BMN001. The data demonstrates that BMN001 reduced HS levels in MPS IIIB dog cerebellum to those seen in unaffected heterozygous carrier dogs.
Figure 7:
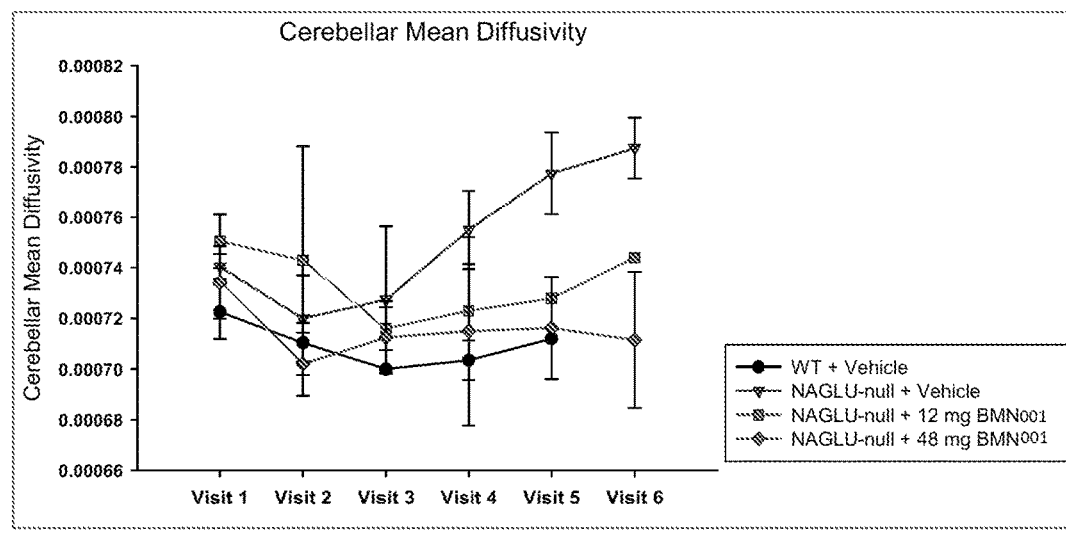
FIG. 7 is a graph showing cerebellar mean diffusivity in control heterozygous Naglu dogs and homozygous Naglu null affected MPS IIIB dogs treated with vehicle, 12 mg BMN001, or 48 mg BMN001.
Figure 8:
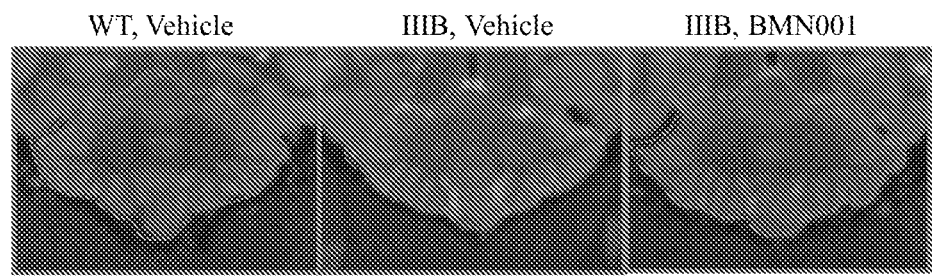
FIG. 8 is a set of MRI images of the cerebellum of wild type vehicle treated dogs and MPS IIIB dogs treated with vehicle or BMN001.

The effect of BMN001 on cerebellar atrophy was also investigated. As seen in FIG. 6, BMN001 caused a significant reduction in cerebellar HS at both doses. Further, both doses of BMN001 attenuated cerebellar white matter decline as measured by diffusion tensor imaging (DTI) (FIG. 7). The attenuation of cerebellar atrophy by BMN001 was also clearly seen in MRI images of wild-type and BMN001 treated MPS IIIB dogs (FIG. 8).

In a separate study, healthy juvenile cynomolgus monkeys weighing approximately 1-2 kg were randomly assigned to one of five dosage groups as follows:

Group 1—ICV vehicle only (5 minutes, 2.5 ml isovolumetric ICV, 0.5 ml/min);
Group 2—30 mg BMN001 (5 minutes, 2.5 ml isovolumetric ICV, 0.5 ml/min);
Group 3—73 mg BMN001 (5 minutes, 2.5 ml isovolumetric ICV, 0.5 ml/min);
Group 4—73 mg BMN001 (240 minutes, 2.5 ml non-isovolumetric ICV, 0.88 ml/hr); and
Group 5—200 mg/kg BMN001 (5 minutes, non-isovolumetric IV, 3 ml/min).

At 48 hours post-dosing, animals were euthanized and specific tissues of the CNS were harvested. Specimens of superficial and deep tissue, relative to the ventricle, for seven brain and three spinal cord regions were collected for biodistribution analyses. These analyses demonstrated that the ICV delivery route enabled direct CNS enzyme replacement with superior biodistribution in the CNS than is achieved via IV administration and that rapid administration of BMN001 following isovolumetric CSF removal is safe and well tolerated in vivo. Finally, comparable and widespread distribution of BMN001 to both superficial and deep CNS tissues was observed from both rapid (i.e., about 5 minutes) isovolumetric administration or slow (i.e., about 240 minutes) non-isovolumetric administration.

Cardiovascular, respiratory and CNS safety pharmacology parameters were assessed in the single and weekly repeat dose monkey toxicity studies. CNS and cardiovascular safety pharmacology parameters were assessed in the biweekly repeat dose studies in WT and NAGLU-null dogs. There were no findings in these studies to indicate there were BMN001-related adverse effects on the CNS, cardiovascular or respiratory systems. No BMN001-related CNS or systemic organ toxicity or toxicity due to exaggerated pharmacology, such as rapid clearance of accumulated lysosomal storage material, has been observed following ICV administration. Furthermore, there was no systemic toxicity, including hypoglycemia, observed after repeat IV administration of BMN001.

For clinical studies conducted in humans, human-equivalent doses were calculated based on scaling of brain mass. The human brain achieves about 75% of adult mass by age 2 and 100% of adult mass by age 5. Given an adult human brain mass of 1400 g and progressive brain atrophy in MPS IIIB patients, an average mass of 1000 g was assumed for the intended patient population. This yields a scaling factor of 10-fold based on an average cynomolgus brain mass of 100 g. Therefore, the safety and efficacy profile of BMN001, as assessed in the current nonclinical program, supports the chronic ICV administration of BMN001 at doses up to 730 mg (as scaled by brain weight) when administered as either a 4-hour infusion or an isovolumetric bolus every week in the intended pediatric patient population.

Example 3—BMN001 for the Treatment of Sanfilippo B Syndrome (Human Clinical Studies)

This is a phase 1/2, first-in-human, multicenter, multinational, open-label, dose-escalation study in human patients diagnosed with MPS IIIB. BMN001, formulated as described in Example 1 above, is administered weekly by ICV infusion and subjects are evaluated in terms of neurocognitive function, behavior, sleep, quality of life (both of the subject and of the family/caregiver), imaging characteristics and biochemical markers of disease burden. The study's primary objectives are to evaluate the safety and tolerability of BMN001 administered to subjects with MPS IIIB via an ICV reservoir and catheter and to evaluate the impact of BMN001 on cognitive function in human patients with MPS IIIB as assessed by an applicable development quotient (DQ). To assess the impact of treatment on cognitive function, data from human subjects under treatment in this study is compared with data from a related observational study of progressive MPS IIIB symptomology conducted earlier in the same set of human subjects (i.e., the "natural history study").

The current phase 1/2 human clinical study consists of 2 parts. In Part 1, the dose escalation period, 3 human subjects (not previously enrolled in natural history study) each receive at least 4 weekly doses of BMN001 at up to 3 escalating dose levels (30 mg, 100 mg and 300 mg) until the maximum tolerated tested dose (MTTD) is established. In Part 2, the stable dose period, up to 30 human subjects previously enrolled in the natural history study begin a treatment course of weekly BMN001 at the MTTD that continues for 48 weeks. The 3 subjects from Part 1 also move into Part 2, perform the Part 2 Baseline assessments and continue weekly dosing for an additional 48 weeks at the MTTD established in Part 1.

The infusion regimen involves isovolumetric removal of 10 ml of CSF followed by ICV delivery of 10 ml total volume of BMN001 over a time period of from about 5 minutes to about 10 minutes. A rapid infusion rate was chosen for this study to address the specific needs of the MPS IIIB patient population; in particular, these patients often have pronounced behavior problems which would make longer infusion periods logistically challenging. Rapid intraventricular delivery of large volumes (e.g., 10-12 ml) of therapeutics following the removal of isovolumetric amounts of CSF is part of routine practice in the pediatric oncology setting. ICV delivery of a longer period of time, however, may also be employed. In this regard a single ICV administration of BMN001 (which may or may not be isovolumetric) may occur over a time period of at least 5, 10, 15, 20, 25, 30, 45, 60, 90, 120, 150, 180, 210 or 240 minutes, or more.

Study procedures performed at Baseline in Part 1 and at Baseline and Weeks 12, 24, 36 and 48 in Part 2 include the Vineland Adaptive Behavior Scales, 2nd Edition (VABS-II), either the Bayley Scales of Infant Development, 3rd Edition (BSID-III) or the Kaufman Assessment Battery for Children, 2nd Edition (KABC-II) and the Sanfilippo Behavior Rating Scale (SBRS). Additional study procedures to be performed during both Part 1 and Part 2 Baseline visits and at Weeks 24 and 48 in Part 2 include the Infant Toddler Quality of Life questionnaire (ITQOL) or Child Health Questionnaire Parent Form (CHQ-PF50), the Children's Sleep Habits Questionnaire (CSHQ), the Parenting Stress Index, the PEDIATRIC QUALITY OF LIFE INVENTORY™ (PEDSQL™) Family Impact Module, MRI (under anesthesia) of the brain and abdomen and a brainstem auditory evoked response (BAER) assessment.

Figure 9:
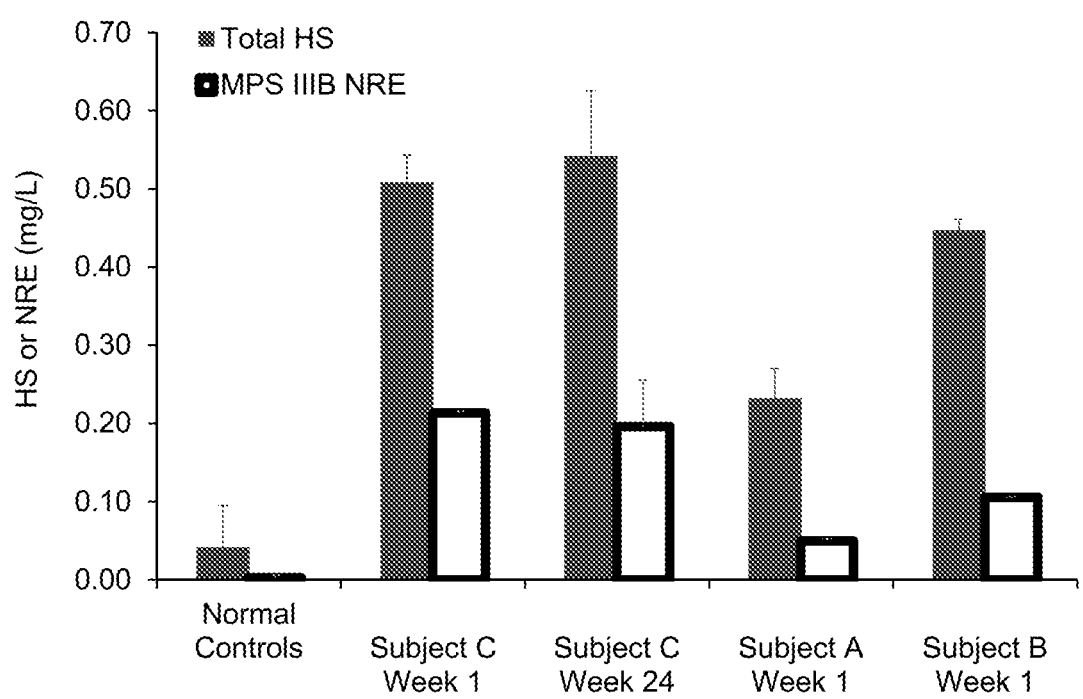
FIG. 9 is a bar graph showing that untreated MPS IIIB patients have elevated Heparan Sulfate (HS) and MPS IIIB-specific HS non-reducing end (NRE) in the cerebrospinal fluid (CSF). The dashed vertical lines show the average normal CSF levels of HS and NRE (0.05 mg/L and 0.0025 mg/L respectively). This data was collected over a period of at least 24 weeks to understand the natural history of the disease. Where available data from early and late time-points in the natural history are shown.

A total of three subjects received at least 8 doses of 30 mg QW BMN001 and at least 3 doses of 100 mg QW. As part of this study, the subjects were monitored over the course of at least 24 weeks prior treatment initiation to understand the natural history of disease progression. The baseline levels of Heparan Sulfate (HS) and MPS IIIB-specific HS non-reducing end (NRE) were measured in the cerebrospinal fluid (CSF) for each patient before and after treatment. As shown in FIG. 9, prior to treatment three subjects (A, B, and C) had extremely elevated HS and NRE compared to non-disease (normal) controls. However, treatment with BMN001 induced marked and sustained decreases in both HS and NRE in both subject A and B (FIG. 10) (subject C enrolled later in the study and data was not yet available). BMN001 was well tolerated with no serious adverse events related to treatment.

These findings demonstrate that BMN001 can be administered safely into the ventricular space via isovolumetric bolus infusion and that this treatment approach leads to a marked pharmacodynamic response in the CNS of MPS IIIB patients.

Example 4—Reformulation of BMN001

Physical stress of formulations containing BMN001 were found to cause the formation of aggregates and/or multimers of the active fusion protein. Aggregates and/or multimers are undesirable in drug products because they likely lower the effective concentration of drug, may cause clogging of in-line filters during administration, and may elicit unwanted immune response to the drug product. Accordingly, additional work was done to identify formulations that were resistant to aggregation and/or multimer formation in response to physical stress. To this end, various excipients were screened for their effect on aggregate/multimer formation (see Table 2). Formulations containing each of these excipients was subjected to physical stress—recirculation pumping—and aggregation was measured by differential scanning calorimetry (DSC) and static light scattering (SLS).

TABLE 2

Excipients Tested for Aggregate Reduction

| EXCIPIENT | CONCENTRATION | CATEGORY | ENDOGENOUS | REDUCED AGGREGATION |
| --- | --- | --- | --- | --- |
| N-acetylglucosamine (GlcNAc) | 4% w/v (180 mM) | NAGLU product | Yes | Yes |
| Glucose | 4% w/v (222 mM) | Sugar | Yes | Yes |
| Sucrose | 8% w/v (234 mM) | Sugar | No | Yes |
| Trehalose | 8% w/v (212 mM) | Sugar | No | Yes |
| Sorbitol | 4% w/v (220 mM) | Sugar Alcohol | No | Yes |
| Arginine | 150 mM | Amino Acid | Yes | No |
| Histidine | 150 mM | Amino Acid | Yes | No |
| Glycine | 150 mM | Amino Acid | Yes | No |
| Glutamic Acid | 25 mM | Amino Acid | Yes | No |
| Glutamine | 150 mM | Amino Acid | Yes | No |
| Polysorbate 20 | 0.1% w/v | Detergent | No | Yes |
| Poloaxamer 188 | 0.1% w/v | Detergent | No | Yes |
| Lecithin | 0.0001% w/v | Phospholipid | Yes | No |

As shown in Table 2, N-acetylglucosamine, glucose, sucrose, trehalose, sorbitol, polysorbate 20, and poloaxamer 188 were found to reduce aggregate/multimer formation. Of these, trehalose and polysorbate 20, were selected as lead candidate excipients for further work.

Figure 11A:
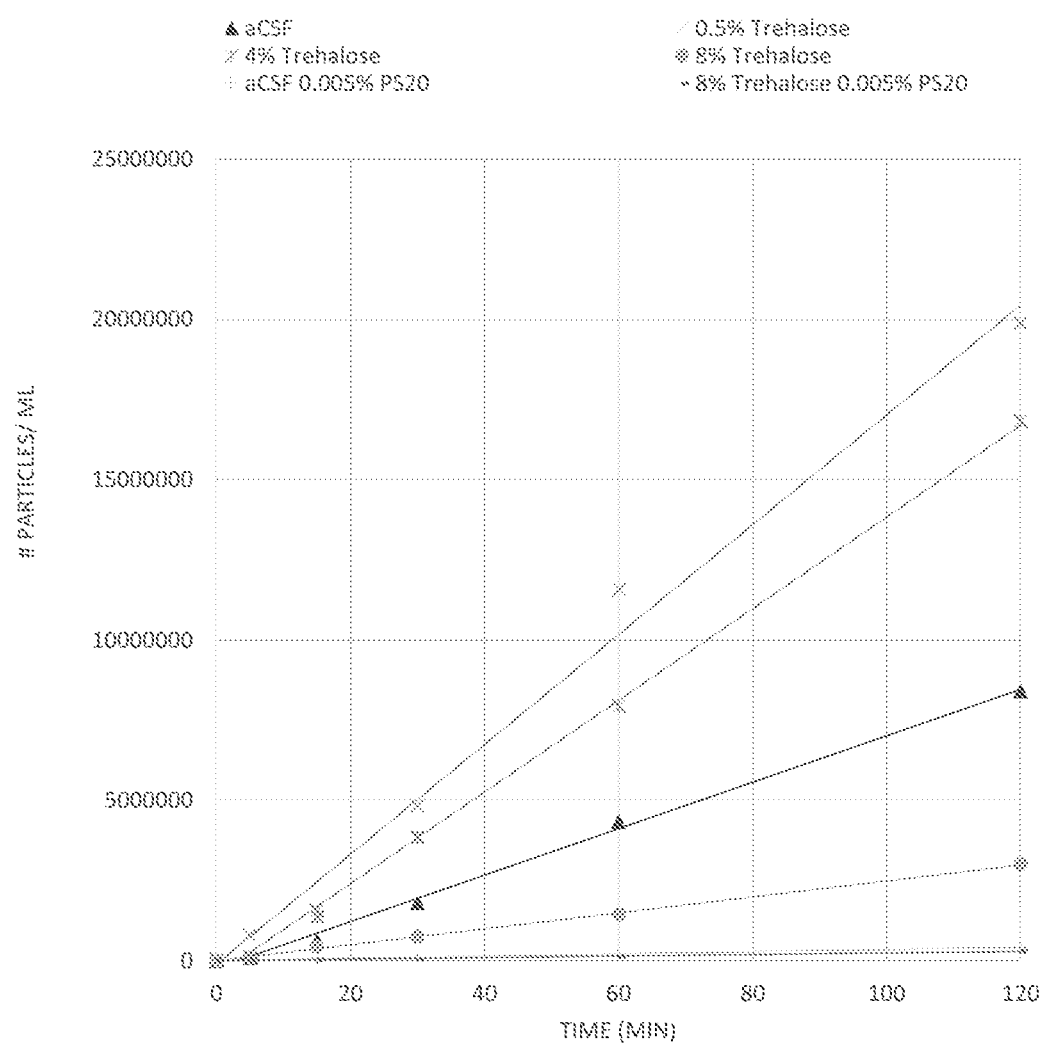
FIGS. 11A and 11B are graphs showing the effects of trehalose and trehalose-polysorbate 20 combination on aggregate particle formation following pumping stress of BMN001 containing formulations.
Figure 11B:
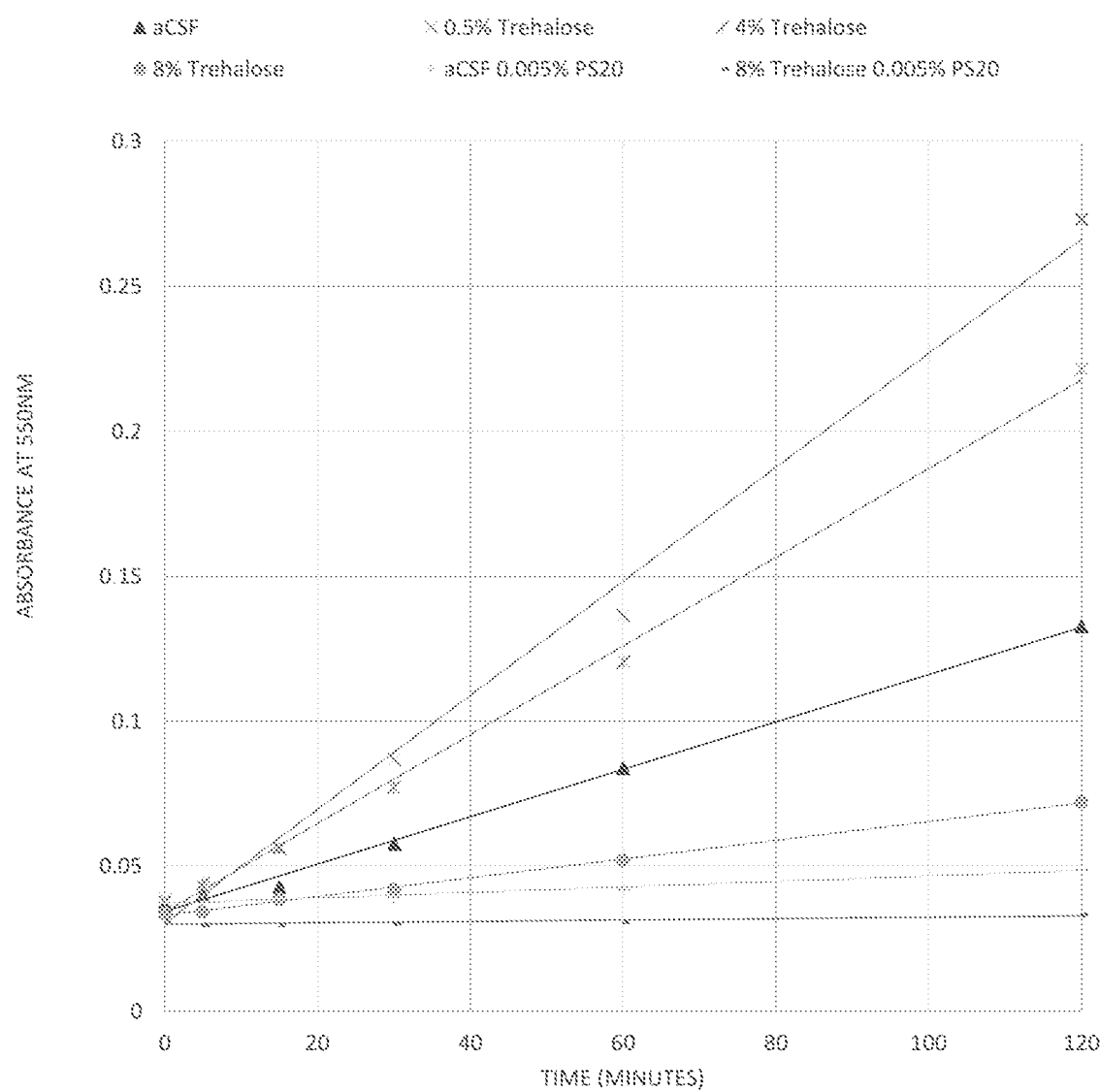

Formulations containing various concentrations of trehalose and/or polysorbate 20 were generated in a base containing sodium phosphate dibasic heptahydrate, sodium phosphate monobasic monohydrate, and sodium chloride. These were then tested for their ability to reduce aggregates/multimers created by recirculation pumping, four passes of pumping, and freeze/thaw cycling (−40° C./25° C. for 20 cycles). In addition, each formulation was tested for stability at accelerated temperatures of 40° C. and 25° C. For each condition, aggregation was measured by visible and sub-visible particle count, solution turbidity (OD550), particle size homogeneity, and percent multimers. As shown in FIGS. 11A and 11B, trehalose reduced particle formation in a dose dependent manner. In addition, the combination of trehalose and polysorbate 20 had the strongest effect on particle formation reduction. Similar results were observed measuring particle formation after each of four passes through a pump, with the combination of both trehalose and polysorbate 20 showing the greatest reduction in particle count (Tables 3 and 4).

TABLE 3

Particles per ml after each stage of pump stress, Trehalose or Polysorbate 20.

| Formulation | Before | Pass 1 | Pass 2 | Pass 3 | Pass 4 |
|---|---|---|---|---|---|
| No Trehalose No PS20* | 50,520 | 49,853 | 138,709 | 239,257 | 385,098 |
| 0.005% PS20 | 55,128 | 51,523 | 74,063 | 88,344 | 118,344 |
| 8% Trehalose | 43,643 | 25,034 | 76,281 | 172,005 | 269,737 |
| 4% Trehalose | 28,511 | 15,703 | 87,551 | 190,998 | 387,826 |

*PS20 is polysorbate 20.

TABLE 4

Particles per ml after each stage of pump stress, Trehalose and Polysorbate 20.

| Formulation | Before | Pass 1 | Pass 2 | Pass 3 | Pass 4 |
|---|---|---|---|---|---|
| No Trehalose No PS20* | 2188 | 9207 | 151,514 | 353,469 | 528,347 |
| 0.005% PS20 | 3549 | 3558 | 125,017 | 212,017 | 276,984 |
| 8% Trehalose 0.005% PS20 | 2961 | 2669 | 40,200 | 88,129 | 122,931 |

*PS20 is polysorbate 20.

Figure 12:
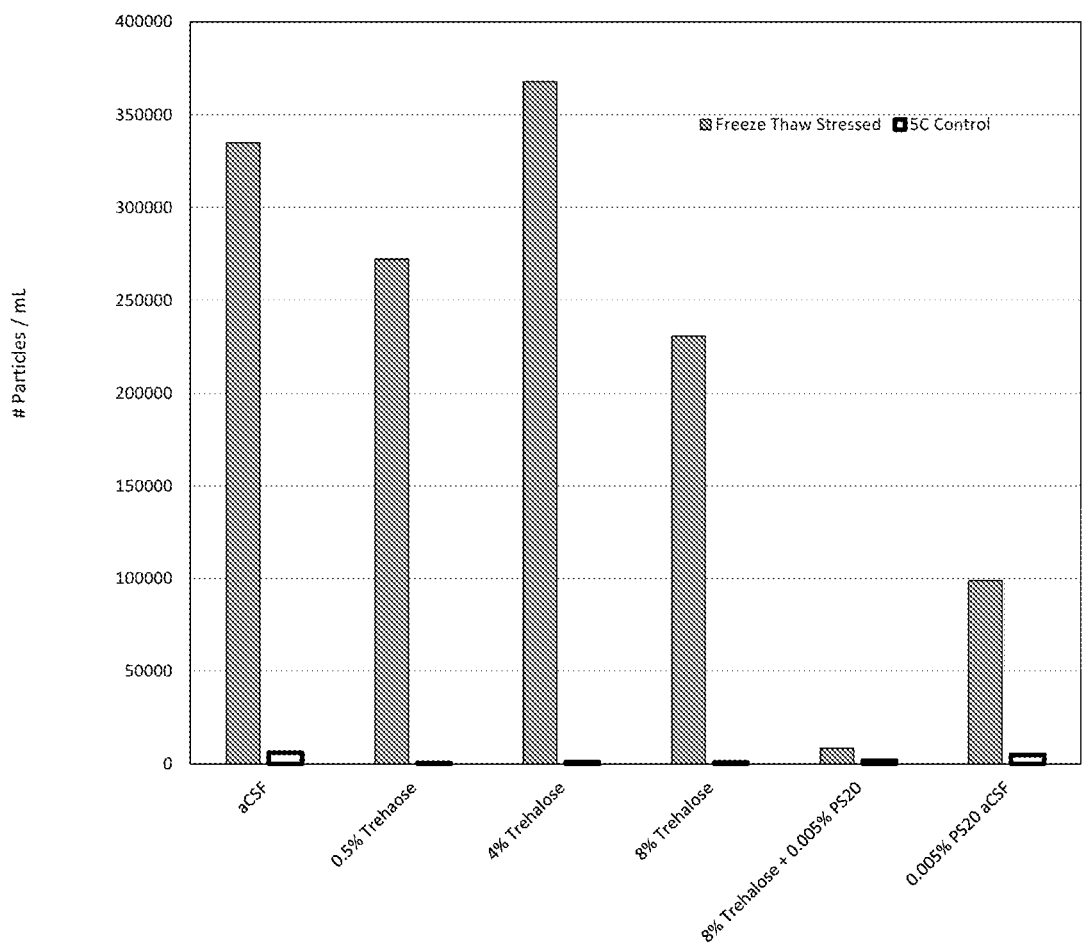
FIG. 12 is a graph showing the effects of trehalose and trehalose-polysorbate 20 combination on aggregate particle formation following freeze thaw stress of BMN001 containing formulations. Artificial cerebrospinal fluid (aCSF) is BMN001 formulated without trehalose or polysorbate 20.

After finding an additive or synergistic effect of the combination of trehalose and polysorbate 20 on inhibiting particle formation in response to pumping stress, a number of trehalose/polysorbate 20 combinations were tested. As shown in Table 5, increasing the amount of either trehalose or polysorbate 20 in the combination decreased the amount of particles formed, with the greatest reduction seen in the combination with the highest trehalose and polysorbate 20 (8% trehalose and 0.005% polysorbate 20). The combination of trehalose and polysorbate 20 was also more effective in the reduction of aggregates formed by twenty freeze/thaw cycles than trehalose or polysorbate 20 alone (FIG. 12). As summarized in Table 6, the excipients trehalose and trehalose in combination with polysorbate 20 effectively reduced BMN001 aggregate and multimer formation relative to the original formulation.

TABLE 5

Effect of varying trehalose/polysorbate 20 combinations on particle formation (particles per ml).

| Formulation | Before | Pass 1 | Pass 2 | Pass 3 | Pass 4 |
|---|---|---|---|---|---|
| No Trehalose No PS20* | 5,214 | 2,871 | 30,688 | 94,475 | 185,233 |
| 4% Trehalose 0.0025% PS20 | 3,701 | 2,369 | 17,674 | 40,193 | 80,759 |
| 4% Trehalose 0.005% PS20 | 7,610 | 1,238 | 7,032 | 16,271 | 28,738 |
| 8% Trehalose 0.00125% PS20 | 8,105 | 4,357 | 46,255 | 81,841 | 116,240 |
| 8% Trehalose 0.0025% PS20 | 7,420 | 9,788 | 14,931 | 33,415 | 51,841 |
| 8% Trehalose 0.005% PS20 | 3,281 | 1,426 | 11,109 | 11,109 | 20,386 |

*PS20 is polysorbate 20.

TABLE 6

Summary of Excipient Effects on Aggregate and Multimer Reduction (percent reduction)

| Formulation | Pumping Model Aggregate Reduction | Freeze/Thaw Aggregate Reduction | Freeze/Thaw Multimer Reduction |
|---|---|---|---|
| 8% Trehalose | 32% | 30% | 100% |
| 8% Trehalose and 0.005% PS20 | 90% | 100% | 100% |
| 8% Trehalose and 0.0025% PS20 | 75% | 100% | 100% |
| 8% Trehalose and 0.001% PS20 | 40% | 100% | 100% |
| 4% Trehalose and 0.005% PS20 | 88% | 100% | 100% |
| 4% Trehalose and 0.0025% PS20 | 57% | 100% | 100% |

From these excipient studies, two additional formulations were identified for use in clinical trials. A formulation containing BMN001 at a concentration of about 30 mg/ml, sodium phosphate dibasic heptahydrate at a concentration of about 0.19 mg/ml, sodium phosphate monobasic monohydrate at a concentration of about 0.04 mg/ml, sodium chloride at a concentration of about 0.88 mg/ml, and trehalose at a concentration of about 8% (w/v), at a pH of about 7.0. And a formulation containing BMN001 at a concentration of about 30 mg/ml, sodium phosphate dibasic heptahydrate at a concentration of about 0.19 mg/ml, sodium phosphate monobasic monohydrate at a concentration of about 0.04 mg/ml, sodium chloride at a concentration of about 5 mg/ml, trehalose at a concentration of about 4% (w/v), and polysorbate 20 at a concentration of about 0.005%, at a pH of about 7.0.

EQUIVALENTS

Those skilled in the art will recognize, or be able to ascertain using no more than routine experimentation, many equivalents to the specific embodiments of the disclosure described herein. The scope of the present disclosure is not intended to be limited to the above Description, but rather is as set forth in the appended claims. The articles "a", "an", and "the" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure also includes embodiments in which more than one, or all, of the group members are present in, employed in, or otherwise relevant to a given product or process. Furthermore, it is to be understood that the disclosure encompasses variations, combinations, and permutations in which one or more limitations, elements, clauses, descriptive terms, etc., from one or more of the claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the disclosure, or aspects of the disclosure, is/are referred to as comprising particular elements, features, etc., certain embodiments of the disclosure or aspects of the disclosure consist, or consist essentially of, such elements, features, etc. For purposes of simplicity those embodiments have not in every case been specifically set forth herein. It should also be understood that any embodiment of the disclosure, e.g., any embodiment found within the prior art, can be explicitly excluded from the claims, regardless of whether the specific exclusion is recited in the specification.

It should also be understood that, unless clearly indicated to the contrary, in any methods claimed herein that include more than one act, the order of the acts of the method is not necessarily limited to the order in which the acts of the method are recited, but the disclosure includes embodiments in which the order is so limited. Furthermore, where the claims recite a composition, the disclosure encompasses methods of using the composition and methods of making the composition. Where the claims recite a composition, it should be understood that the disclosure encompasses methods of using the composition and methods of making the composition.

All publications and patent documents cited in this application are incorporated by reference in their entirety to the same extent as if the contents of each individual publication or patent document were incorporated herein.

What is claimed:

1. A method for reducing glycosaminoglycan (GAG) storage in one or more CNS tissues of a subject suffering from Mucopolysaccharidosis Type IIIB, comprising administering to the subject a therapeutically effective amount of a formulation comprising
   (a) a fusion protein comprising an alpha-N-acetylglucosaminidase (Naglu) enzyme having detectable Naglu enzyme activity and an amino acid sequence that is at least 95% identical to SEQ ID NO: 1 and an insulin-like growth factor II (IGF-II) peptide tag having at least 90% sequence identity to SEQ ID NO: 2, and a spacer peptide located between the Naglu enzyme and the IGF-II peptide tag, the spacer peptide having at least 90% sequence identity to SEQ ID NO: 4 and the fusion protein is at a concentration of from 25 mg/ml to 35 mg/ml; and
   (b) one or more components selected from the group consisting of a buffering agent, an isotonicity agent, an electrolyte agent, and an anti-adsorbent agent.

2. The method of claim 1, wherein the GAG is heparan sulfate.

3. The method of claim 1, wherein GAG storage is reduced in a lysosome of a cell in the one or more CNS tissues, wherein the one or more CNS tissues are selected from the group consisting of gray matter, white matter, periventricular areas, meninges, pia-arachnoid, deep tissues in the cerebral cortex, neocortex, cerebellum, caudate/putamen region, molecular layer, deep regions of the pons or medulla, midbrain, and spinal cord neurons.

4. The method of claim 1, wherein the formulation is administered to the subject as an intracerebroventricular administration.

5. The method of claim 4, wherein the intracerebroventricular administration is isovolumetric.

6. The method of claim 4, wherein the intracerebroventricular administration is administered to the subject over a time period of about 5 minutes to about 240 minutes.

7. The method of claim 6, wherein the intracerebroventricular administration is administered to the subject over a time period of about 5 minutes to about 10 minutes.

8. The method of claim 1, wherein the formulation is administered to the subject weekly.

9. The method of claim 8, wherein the formulation is administered to the subject weekly for at least 24 weeks.

10. The method of claim 8, wherein the formulation is administered to the subject weekly for at least 48 weeks.

11. The method of claim 3, wherein the administering to the subject of the therapeutically effective amount of the formulation results in an improvement in at least one symptom of Mucopolysaccharidosis Type IIIB.

12. The method of claim 1, wherein the fusion protein comprises the amino acid sequence of SEQ ID NO: 1 or 5.

13. The method of claim 1, wherein the formulation comprises components buffering agent, isotonicity agent, and electrolyte agent.

14. The method of claim 13, wherein the formulation comprises sodium phosphate dibasic heptahydrate, sodium phosphate monobasic monohydrate, sodium chloride, and trehalose, and wherein the fusion protein comprises the amino acid sequence of SEQ ID NO: 5.

15. The method of claim 14, wherein the sodium phosphate dibasic heptahydrate is at a concentration of from about 0.15 mg/ml to about 0.25 mg/ml, the sodium phosphate monobasic monohydrate is at a concentration of from about 0.03 mg/ml to about 0.05 mg/ml, the sodium chloride is at a concentration of from about 0.8 mg/ml to about 1.0 mg/ml, and the trehalose is at a concentration of from about 7% (w/v) to about 9% (w/v), the formulation having a pH in the range of about 6.5 to about 7.5.

16. The method of claim 13, wherein the formulation comprises sodium phosphate dibasic heptahydrate, sodium phosphate monobasic monohydrate, sodium chloride, potassium chloride, magnesium chloride hexahydrate, calcium chloride dihydrate, and wherein the fusion protein comprises the amino acid sequence of SEQ ID NO: 5.

17. The method of claim 16, wherein the sodium phosphate dibasic heptahydrate is at a concentration of from about 0.15 mg/ml to about 0.25 mg/ml, the sodium phosphate monobasic monohydrate is at a concentration of from about 0.03 mg/ml to about 0.05 mg/ml, the sodium chloride is at a concentration of from about 8 mg/ml to about 9 mg/ml, the potassium chloride is at a concentration of from about 0.15 mg/ml to about 0.3 mg/ml, the magnesium chloride hexahydrate is at a concentration of from about 0.1 mg/ml to about 0.2 mg/ml, and the calcium chloride dihydrate is at a concentration of from about 0.15 mg/ml to about 0.3 mg/ml, the formulation having a pH in the range of about 6.5 to about 7.5.

18. The method of claim 17, wherein the sodium phosphate dibasic heptahydrate is at a concentration of from 0.15 mg/ml to 0.25 mg/ml, the sodium phosphate monobasic monohydrate is at a concentration of from 0.03 mg/ml to 0.05 mg/ml, the sodium chloride is at a concentration of from 8 mg/ml to 9 mg/ml, the potassium chloride is at a concentration of from 0.15 mg/ml to 0.3 mg/ml, the magnesium chloride hexahydrate is at a concentration of from 0.1 mg/ml to 0.2 mg/ml, and the calcium chloride dihydrate is at a concentration of from 0.15 mg/ml to 0.3 mg/ml, the formulation having a pH in the range of 6.5 to 7.5.

19. The method of claim 18, wherein the fusion protein is at a concentration of about 30 mg/ml, the sodium phosphate dibasic heptahydrate is at a concentration of about 0.19 mg/ml, the sodium phosphate monobasic monohydrate is at a concentration of about 0.04 mg/ml, the sodium chloride is at a concentration of about 8.66 mg/ml, the potassium chloride is at a concentration of about 0.22 mg/ml, the magnesium chloride hexahydrate is at a concentration of about 0.16 mg/ml, and the calcium chloride dihydrate is at a concentration of about 0.21 mg/ml, the formulation having a pH of about 7.0.

20. The method of claim 19, wherein the fusion protein is at a concentration of 30 mg/ml, the sodium phosphate dibasic heptahydrate is at a concentration of 0.19 mg/ml, the sodium phosphate monobasic monohydrate is at a concentration of 0.04 mg/ml, the sodium chloride is at a concentration of 8.66 mg/ml, the potassium chloride is at a concentration of 0.22 mg/ml, the magnesium chloride hexahydrate is at a concentration of 0.16 mg/ml, and the calcium chloride dihydrate is at a concentration of 0.21 mg/ml, the formulation having a pH of 7.0.

* * * * *

UNITED STATES PATENT AND TRADEMARK OFFICE
CERTIFICATE OF CORRECTION

PATENT NO. : 11,345,904 B2  
APPLICATION NO. : 16/078546  
DATED : May 31, 2022  
INVENTOR(S) : Moshashaee et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 342 days.

Signed and Sealed this  
Tenth Day of June, 2025

Coke Morgan Stewart  
*Acting Director of the United States Patent and Trademark Office*

SEQUENCE LISTING

```
<160> NUMBER OF SEQ ID NOS: 5

<210> SEQ ID NO 1
<211> LENGTH: 720
<212> TYPE: PRT
<213> ORGANISM: Homo sapiens
<220> FEATURE:
<221> NAME/KEY: MISC_FEATURE
<223> OTHER INFORMATION: Naglu protein

<400> SEQUENCE: 1

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
        35                  40                  45

Ala Ala Arg Val Arg Val Arg Gly Ser Thr Gly Val Ala Ala Ala Ala
    50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Gln Asn Val
            100                 105                 110

Cys Thr Gln Ser Tyr Ser Phe Val Trp Trp Asp Trp Ala Arg Trp Glu
        115                 120                 125

Arg Glu Ile Asp Trp Met Ala Leu Asn Gly Ile Asn Leu Ala Leu Ala
    130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
            180                 185                 190
```

```
Pro Ser Trp His Ile Lys Gln Leu Tyr Leu Gln His Arg Val Leu Asp
        195                 200                 205

Gln Met Arg Ser Phe Gly Met Thr Pro Val Leu Pro Ala Phe Ala Gly
    210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
                260                 265                 270

Leu Arg Glu Leu Ile Lys Glu Phe Gly Thr Asp His Ile Tyr Gly Ala
            275                 280                 285

Asp Thr Phe Asn Glu Met Gln Pro Pro Ser Ser Glu Pro Ser Tyr Leu
290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
                325                 330                 335

Phe Trp Gly Pro Ala Gln Ile Arg Ala Val Leu Gly Ala Val Pro Arg
                340                 345                 350

Gly Arg Leu Leu Val Leu Asp Leu Phe Ala Glu Ser Gln Pro Val Tyr
            355                 360                 365

Thr Arg Thr Ala Ser Phe Gln Gly Gln Pro Phe Ile Trp Cys Met Leu
            370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
                420                 425                 430

Ser Leu Met Ala Glu Leu Gly Trp Arg Lys Asp Pro Val Pro Asp Leu
            435                 440                 445

Ala Ala Trp Val Thr Ser Phe Ala Ala Arg Arg Tyr Gly Val Ser His
            450                 455                 460

Pro Asp Ala Gly Ala Ala Trp Arg Leu Leu Arg Ser Val Tyr Asn
465                 470                 475                 480

Cys Ser Gly Glu Ala Cys Arg Gly His Asn Arg Ser Pro Leu Val Arg
                485                 490                 495

Arg Pro Ser Leu Gln Met Asn Thr Ser Ile Trp Tyr Asn Arg Ser Asp
            500                 505                 510

Val Phe Glu Ala Trp Arg Leu Leu Leu Thr Ser Ala Pro Ser Leu Ala
            515                 520                 525

Thr Ser Pro Ala Phe Arg Tyr Asp Leu Leu Asp Leu Thr Arg Gln Ala
            530                 535                 540

Val Gln Glu Leu Val Ser Leu Tyr Tyr Glu Ala Arg Ser Ala Tyr
545                 550                 555                 560

Leu Ser Lys Glu Leu Ala Ser Leu Leu Arg Ala Gly Gly Val Leu Ala
                565                 570                 575

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Ala Val Ser
            595                 600                 605
```

-continued

```
Glu Ala Glu Ala Asp Phe Tyr Gln Asn Ser Arg Tyr Gln Leu Thr
    610             615                 620
Leu Trp Gly Pro Glu Gly Asn Ile Leu Asp Tyr Ala Asn Lys Gln Leu
625                 630                 635                 640
Ala Gly Leu Val Ala Asn Tyr Tyr Thr Pro Arg Trp Arg Leu Phe Leu
                645                 650                 655
Glu Ala Leu Val Asp Ser Val Ala Gln Gly Ile Pro Phe Gln Gln His
            660                 665                 670
Gln Phe Asp Lys Asn Val Phe Gln Leu Glu Gln Ala Phe Val Leu Ser
        675                 680                 685
Lys Gln Arg Tyr Pro Ser Gln Pro Arg Gly Asp Thr Val Asp Leu Ala
690                 695                 700
Lys Lys Ile Phe Leu Lys Tyr Tyr Pro Arg Trp Val Ala Gly Ser Trp
705                 710                 715                 720

<210> SEQ ID NO 2
<211> LENGTH: 60
<212> TYPE: PRT
<213> ORGANISM: Homo sapiens
<220> FEATURE:
<221> NAME/KEY: MISC_FEATURE
<223> OTHER INFORMATION: AA 8-67 of IGF-II

<400> SEQUENCE: 2

Leu Cys Gly Gly Glu Leu Val Asp Thr Leu Gln Phe Val Cys Gly Asp
1               5                   10                  15
Arg Gly Phe Tyr Phe Ser Arg Pro Ala Ser Arg Val Ser Arg Arg Ser
            20                  25                  30
Arg Gly Ile Val Glu Glu Cys Cys Phe Arg Ser Cys Asp Leu Ala Leu
        35                  40                  45
Leu Glu Thr Tyr Cys Ala Thr Pro Ala Lys Ser Glu
    50                  55                  60

<210> SEQ ID NO 3
<211> LENGTH: 60
<212> TYPE: PRT
<213> ORGANISM: Artificial Sequence
<220> FEATURE:
<223> OTHER INFORMATION: Peptide Tag

<400> SEQUENCE: 3

Leu Cys Gly Gly Glu Leu Val Asp Thr Leu Gln Phe Val Cys Gly Asp
1               5                   10                  15
Arg Gly Phe Tyr Phe Ser Arg Pro Ala Ser Arg Val Ser Ala Arg Ser
            20                  25                  30
Arg Gly Ile Val Glu Glu Cys Cys Phe Arg Ser Cys Asp Leu Ala Leu
        35                  40                  45
Leu Glu Thr Tyr Cys Ala Thr Pro Ala Lys Ser Glu
    50                  55                  60

<210> SEQ ID NO 4
<211> LENGTH: 31
<212> TYPE: PRT
<213> ORGANISM: Artificial Sequence
<220> FEATURE:
<223> OTHER INFORMATION: Peptide Linker

<400> SEQUENCE: 4

Gly Ala Pro Gly Gly Ser Pro Ala Pro Ala Pro Thr Pro Ala Pro
1               5                   10                  15
```

```
Ala Pro Thr Pro Ala Pro Ala Gly Gly Gly Pro Ser Gly Ala Pro
            20                  25                  30
```

<210> SEQ ID NO 5
<211> LENGTH: 811
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: BMN001 therapeutic fusion protein

<400> SEQUENCE: 5

```
Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Glu Arg Ala
            20                  25                  30

Leu Ala Ala Lys Pro Gly Leu Asp Thr Tyr Ser Leu Gly Gly Gly
            35                  40                  45

Ala Ala Arg Val Arg Val Arg Gly Ser Thr Gly Val Ala Ala Ala
            50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Gln Asn Val
                100                 105                 110

Cys Thr Gln Ser Tyr Ser Phe Val Trp Trp Asp Trp Ala Arg Trp Glu
                115                 120                 125

Arg Glu Ile Asp Trp Met Ala Leu Asn Gly Ile Asn Leu Ala Leu Ala
130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
                180                 185                 190

Pro Ser Trp His Ile Lys Gln Leu Tyr Leu Gln His Arg Val Leu Asp
                195                 200                 205

Gln Met Arg Ser Phe Gly Met Thr Pro Val Leu Pro Ala Phe Ala Gly
                210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
                260                 265                 270

Leu Arg Glu Leu Ile Lys Glu Phe Gly Thr Asp His Ile Tyr Gly Ala
                275                 280                 285

Asp Thr Phe Asn Glu Met Gln Pro Pro Ser Ser Glu Pro Ser Tyr Leu
                290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
                325                 330                 335
```

```
Phe Trp Gly Pro Ala Gln Ile Arg Ala Val Leu Ala Val Pro Arg
            340                 345                 350

Gly Arg Leu Leu Val Leu Asp Leu Phe Ala Glu Ser Gln Pro Val Tyr
        355                 360                 365

Thr Arg Thr Ala Ser Phe Gln Gly Gln Pro Phe Ile Trp Cys Met Leu
    370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
            420                 425                 430

Ser Leu Met Ala Glu Leu Gly Trp Arg Lys Asp Pro Val Pro Asp Leu
        435                 440                 445

Ala Ala Trp Val Thr Ser Phe Ala Ala Arg Arg Tyr Gly Val Ser His
    450                 455                 460

Pro Asp Ala Gly Ala Ala Trp Arg Leu Leu Arg Ser Val Tyr Asn
465                 470                 475                 480

Cys Ser Gly Glu Ala Cys Arg Gly His Asn Arg Ser Pro Leu Val Arg
                485                 490                 495

Arg Pro Ser Leu Gln Met Asn Thr Ser Ile Trp Tyr Asn Arg Ser Asp
            500                 505                 510

Val Phe Glu Ala Trp Arg Leu Leu Leu Thr Ser Ala Pro Ser Leu Ala
        515                 520                 525

Thr Ser Pro Ala Phe Arg Tyr Asp Leu Leu Asp Leu Thr Arg Gln Ala
    530                 535                 540

Val Gln Glu Leu Val Ser Leu Tyr Tyr Glu Glu Ala Arg Ser Ala Tyr
545                 550                 555                 560

Leu Ser Lys Glu Leu Ala Ser Leu Leu Arg Ala Gly Val Leu Ala
                565                 570                 575

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Val Ser
        595                 600                 605

Glu Ala Glu Ala Asp Phe Tyr Glu Gln Asn Ser Arg Tyr Gln Leu Thr
    610                 615                 620

Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
            660                 665                 670

Gln Phe Asp Lys Asn Val Phe Gln Leu Glu Gln Ala Phe Val Leu Ser
        675                 680                 685

Lys Gln Arg Tyr Pro Ser Gln Pro Arg Gly Asp Thr Val Asp Leu Ala
    690                 695                 700

Lys Lys Ile Phe Leu Lys Tyr Tyr Pro Arg Trp Val Ala Gly Ser Trp
705                 710                 715                 720

Gly Ala Pro Gly Gly Ser Pro Ala Pro Ala Thr Pro Ala Pro
                725                 730                 735

Ala Pro Thr Pro Ala Pro Ala Gly Gly Gly Pro Ser Gly Ala Pro Leu
            740                 745                 750

Cys Gly Gly Glu Leu Val Asp Thr Leu Gln Phe Val Cys Gly Asp Arg
```

-continued

```
                755                 760                 765
Gly Phe Tyr Phe Ser Arg Pro Ala Ser Arg Val Ser Ala Arg Ser Arg
        770                 775                 780

Gly Ile Val Glu Glu Cys Cys Phe Arg Ser Cys Asp Leu Ala Leu Leu
785                 790                 795                 800

Glu Thr Tyr Cys Ala Thr Pro Ala Lys Ser Glu
                805                 810
```